(12) United States Patent
Miazga et al.

(10) Patent No.: US 7,340,309 B2
(45) Date of Patent: Mar. 4, 2008

(54) METHOD AND APPARATUS FOR CONTROLLING THE DEPTH OF PERCUTANEOUS APPLICATIONS

(75) Inventors: Jay Miazga, Seattle, WA (US); Chris Genau, Seattle, WA (US); Paul C. Leonard, Woodinville, WA (US); Bradford Evan Gliner, Sammamish, WA (US)

(73) Assignee: Meagan Medical, Inc., Vancouver, WA (US)

( * ) Notice: Subject to any disclaimer, the term of this patent is extended or adjusted under 35 U.S.C. 154(b) by 701 days.

(21) Appl. No.: 10/735,809

(22) Filed: Dec. 16, 2003

(65) Prior Publication Data

US 2004/0147996 A1    Jul. 29, 2004

Related U.S. Application Data

(60) Provisional application No. 60/433,823, filed on Dec. 16, 2002.

(51) Int. Cl.
*A61N 1/04* (2006.01)
*A61B 17/32* (2006.01)
*A61B 17/34* (2006.01)

(52) U.S. Cl. .................. 607/115; 607/145; 607/146; 600/372; 600/382; 606/167; 606/172; 606/181; 606/184; 606/185

(58) Field of Classification Search ............... 606/172, 606/167, 181, 184–185; 607/115, 145–146; 600/372, 382
See application file for complete search history.

(56) References Cited

U.S. PATENT DOCUMENTS

| | | | | |
|---|---|---|---|---|
| 4,895,147 A | * | 1/1990 | Bodicky et al. | ............. 606/182 |
| 5,613,978 A | * | 3/1997 | Harding | ....................... 606/181 |
| 6,549,797 B1 | * | 4/2003 | Leonard et al. | ............. 600/372 |
| 6,613,064 B2 | * | 9/2003 | Rutynowski et al. | ....... 606/185 |
| 6,645,219 B2 | * | 11/2003 | Roe | ........................... 606/182 |
| 2001/0021869 A1 | | 9/2001 | Bishay et al. | |

OTHER PUBLICATIONS

U.S. Appl. No. 10/735,808, filed Dec. 16, 2003, Jay Miazga et al.
U.S. Appl. No. 10/735,807, filed Dec. 16, 2003, Jay Miazga et al.

(Continued)

*Primary Examiner*—Carl Layno
*Assistant Examiner*—S Johnson
(74) *Attorney, Agent, or Firm*—Blank Rome LLP

(57) ABSTRACT

Methods and apparatuses for deploying percutaneous probes. An apparatus in accordance with one embodiment of the invention includes a housing and a percutaneous probe having a sharp end and positioned within the housing. The percutaneous probe is movable relative to the housing between a stowed position and at least one of a first deployed position and a second deployed position. The percutaneous probe can project from the housing by a first distance when in the first deployed position and a second distance greater than the first distance when in the second deployed position. A depth control device can operatively couple to the percutaneous probe and can have a first configuration to allow the percutaneous probe to be moved to the first deployed position and a second configuration to allow the percutaneous probe to be moved to the second deployed position.

35 Claims, 29 Drawing Sheets

OTHER PUBLICATIONS

Ghoname et al., "Percutaneous Electrical Nerve Stimulation for Low Back Pain," JAMA 281:818-23 (1999).

Ghoname et al., "The Effect of Stimulus Frequency on the Analgesic Response to Percutaneous Electrical Nerve Stimulation in Patients with Chronic Low Back Pain," Anesth. Analg. 88:841-6 (1999).

Ahmed et al., "Percutaneous Electrical Nerve Stimulation (PENS): A Complementary Therapy for the Management of Pain Secondary to Bony Metastasis," Clinical Journal of Pain 14:320-3 (1998).

Ahmed et al., "Percutaneous Electrical Nerve Stimulation: An Alternative to Antiviral Drugs for Herpes Zoster," Anesth. Analg. 87:911-4 (1998).

European Patent Office, Extended European Search Report, dated May 3, 2007, issued in European Application No. 05108878, filed Dec. 16, 2003.

* cited by examiner

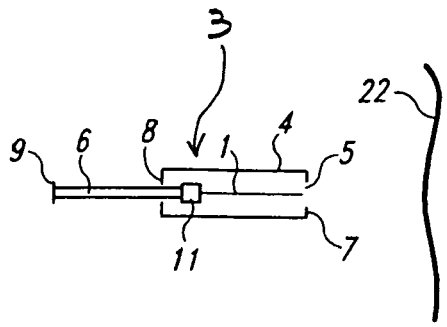
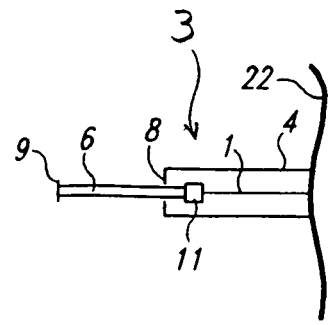
Fig. 1A  Fig. 1B
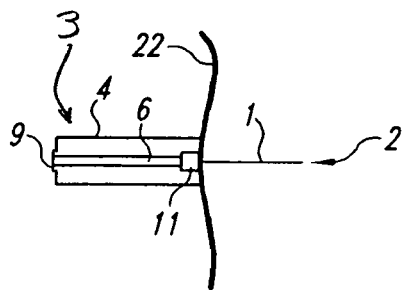
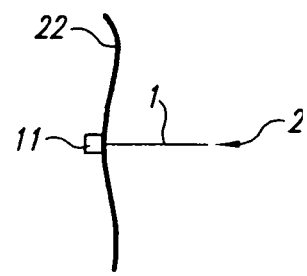
Fig. 1C  Fig. 1D
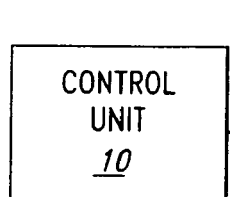
Fig. 1E
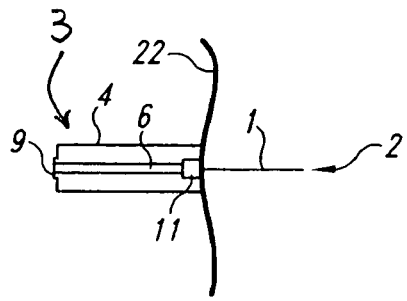
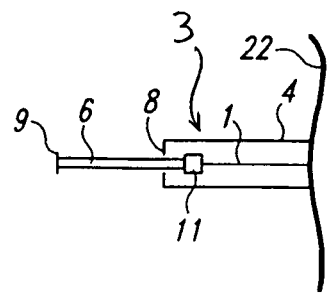
Fig. 1F  Fig. 1G

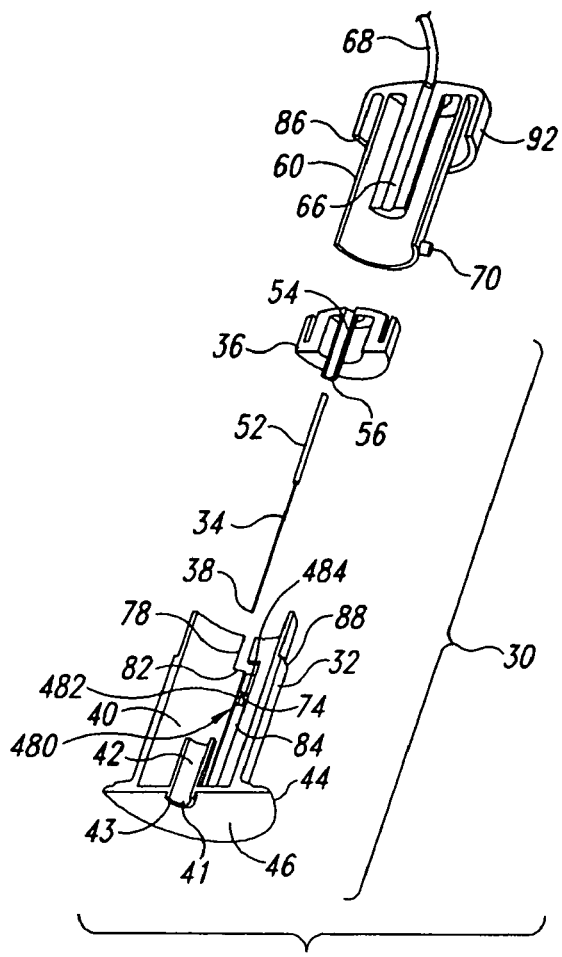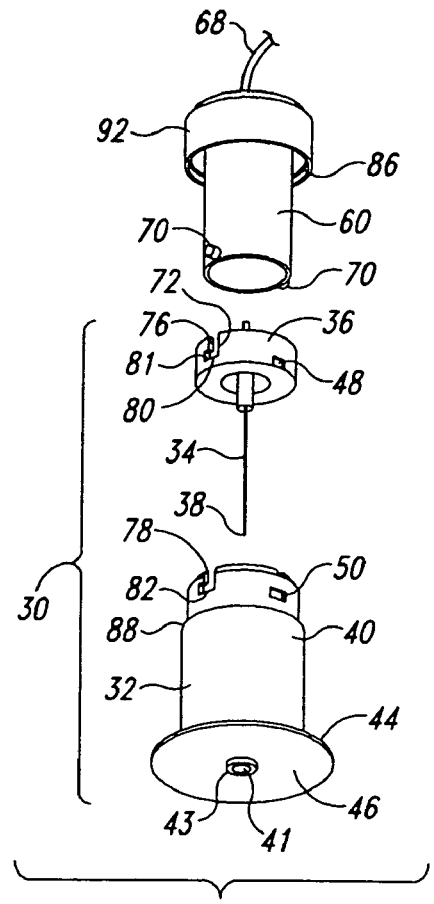
Fig. 4
Fig. 5
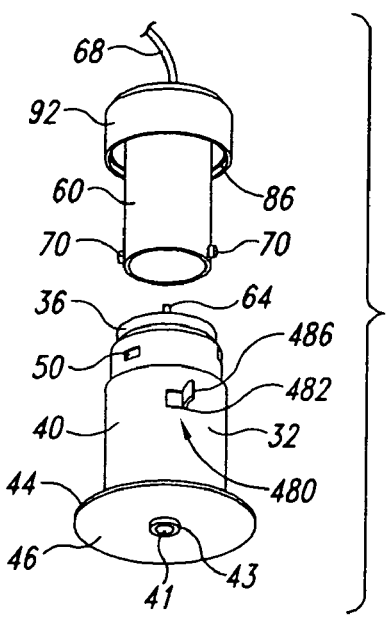
Fig. 6

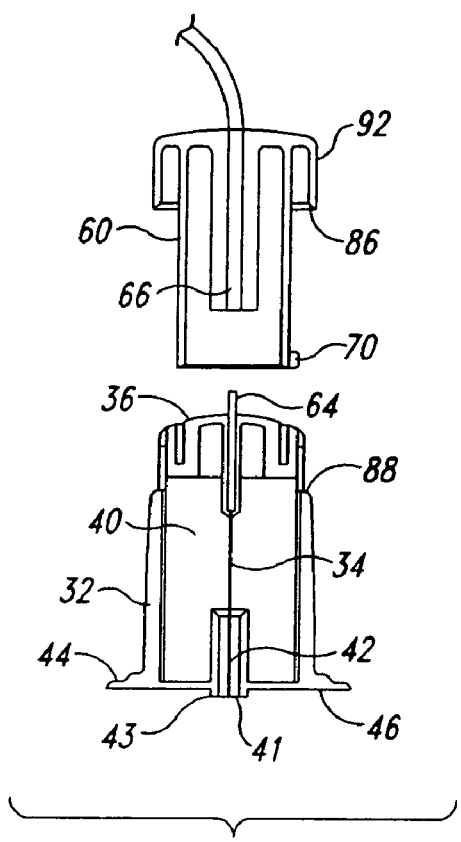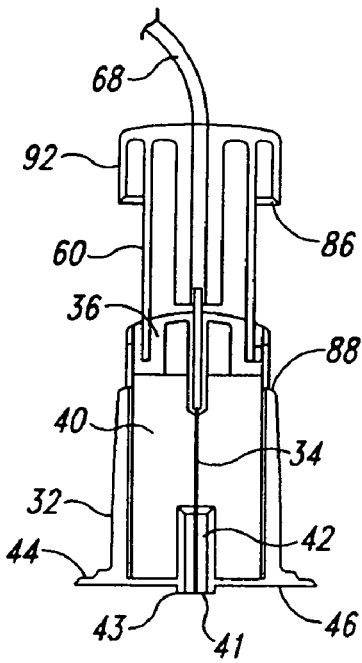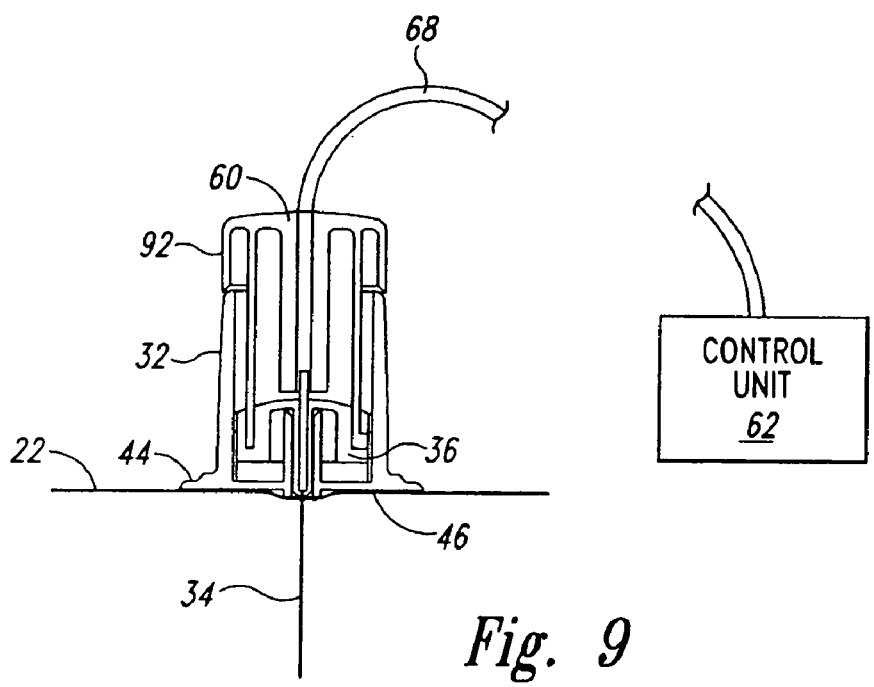
Fig. 7
Fig. 8
Fig. 9

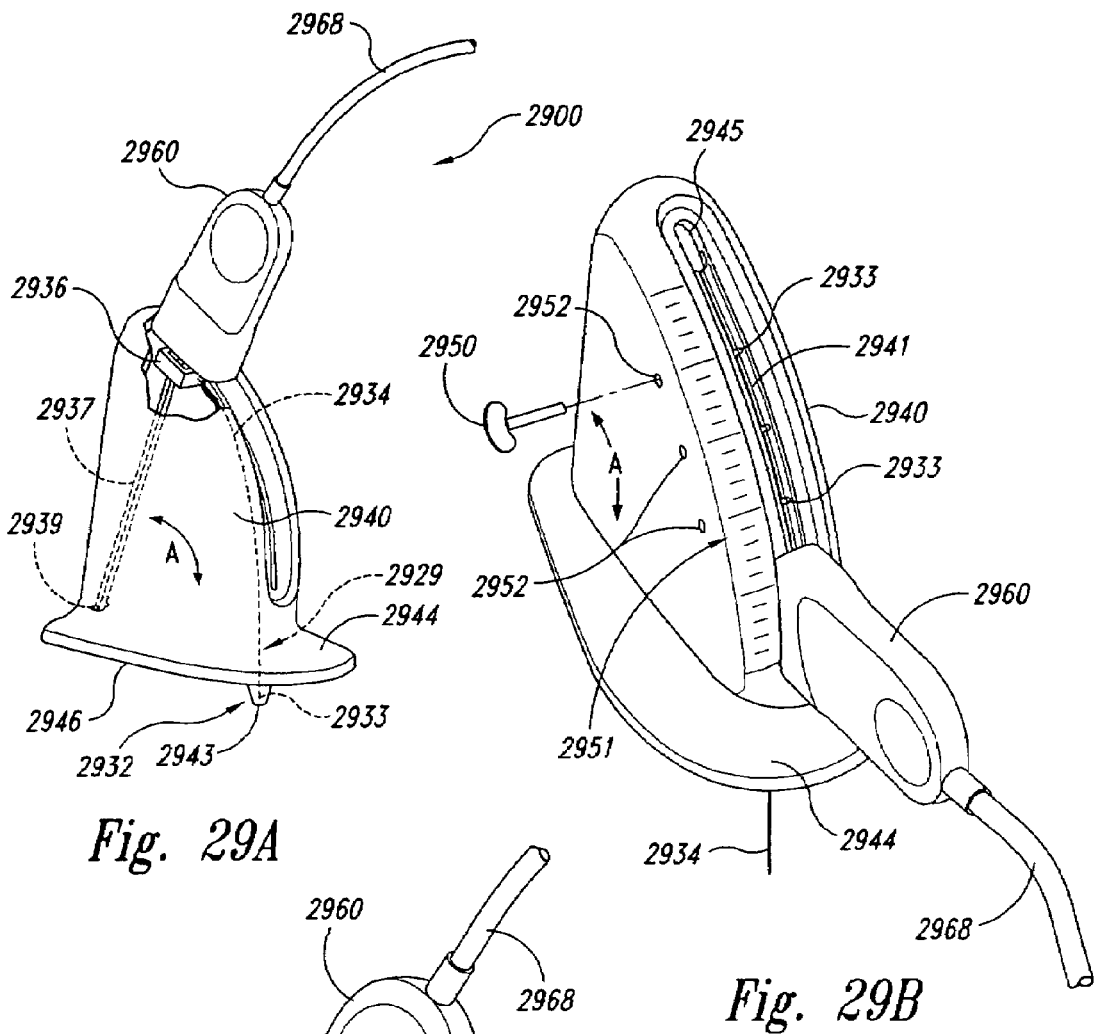
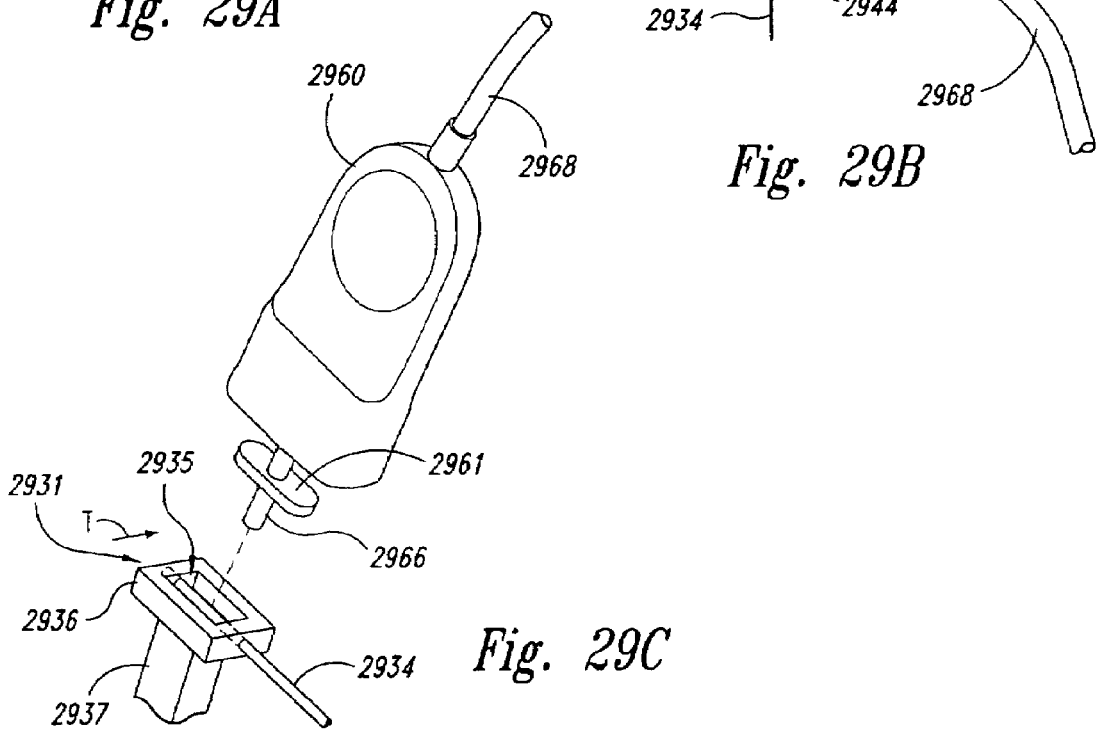
Fig. 29A
Fig. 29B
Fig. 29C

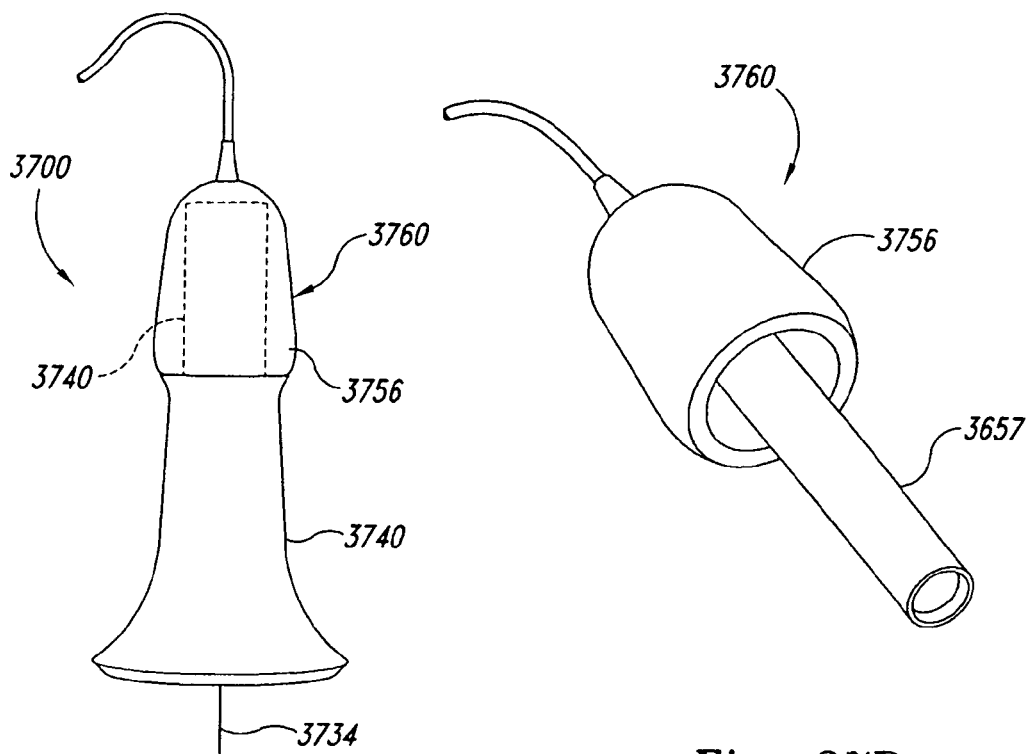
Fig. 37A
Fig. 37B
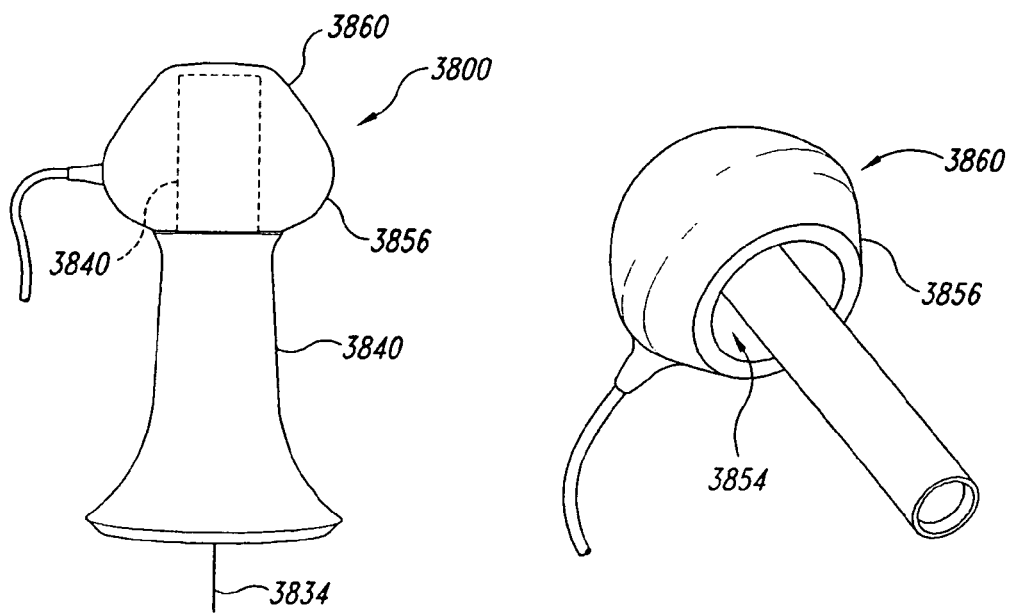
Fig. 38A
Fig. 38B

METHOD AND APPARATUS FOR CONTROLLING THE DEPTH OF PERCUTANEOUS APPLICATIONS

REFERENCE TO RELATED APPLICATION

This application claims the benefit of U.S. Provisional Patent Application No. 60/433,823, filed Dec. 16, 2002, whose disclosure is hereby incorporated by reference in its entirety into the present disclosure.

TECHNICAL FIELD

The present invention relates to methods and apparatuses for percutaneous applications, including methods and apparatuses for controlling the depth to which a percutaneous probe is deployed.

BACKGROUND

Electrical therapy has long been used in medicine to treat pain and other conditions. For example, transcutaneous electrical nerve stimulation (TENS) systems deliver electrical energy through electrode patches placed on the surface of a patient's skin to treat pain in tissue beneath and around the location of the patches. The efficacy of TENS systems in alleviating pain is questionable at best, however.

More recently, a technique in which electrodes are placed through the patient's skin into the target tissue has been proposed. Percutaneous Neuromodulation Therapy ("PNT") (also sometimes called Percutaneous Electrical Nerve Stimulation or "PENS") using percutaneously placed electrodes achieves significantly better pain relief results than TENS treatments using skin surface electrodes. This therapy is described in Ghoname et al., "Percutaneous Electrical Nerve Stimulation for Low Back Pain," JAMA 281:818-23 (1999); Ghoname et al.; "The Effect of Stimulus Frequency on the Analgesic Response to Percutaneous Electrical Nerve Stimulation in Patients with Chronic Low Back Pain," Anesth. Analg. 88:841-6 (1999); Ahmed et al., "Percutaneous Electrical Nerve Stimulation (PENS): A Complementary Therapy for the Management of Pain Secondary to Bony Metastasis," Clinical Journal of Pain 14:320-3 (1998); and Ahmed et al., "Percutaneous Electrical Nerve Stimulation: An Alternative to Antiviral Drugs for Herpes Zoster," Anesth. Analg. 87:911-4 (1998). The contents of these references are incorporated herein by reference.

One drawback with some existing PNT techniques is that it can be difficult for practitioners to accurately determine how far the percutaneous electrode is inserted beneath the patient's skin. As a result, the practitioner may not position the electrode at the most effective location, and accordingly may not deliver treatment in an optimal fashion. Another drawback with some existing PNT techniques is that the electrode can be difficult to manipulate, keep track of, and/or work around, particularly when multiple electrodes are used simultaneously on a relatively small portion of the patient's body.

SUMMARY

The present invention is directed to methods and apparatuses for percutaneous applications. An apparatus in accordance with one aspect of the invention includes a housing and a percutaneous probe having a sharp end wherein the percutaneous probe is positioned within the housing. The percutaneous probe can be movable relative to the housing between a stowed position and at least one of a first deployed position and a second deployed position. The percutaneous probe projects from the housing by a first distance when in the first deployed position, and projects from the housing by a second distance greater than the first distance when in the second deployed position. A depth control device can operatively couple to the percutaneous probe and have a first configuration to allow the percutaneous probe to move to the first deployed position, and a second configuration to allow the percutaneous probe to move to the second deployed position.

In a further aspect of the invention, the depth control device can include a pre-adjustable portion configured to be movable between a first stop position and a second stop position without moving the percutaneous probe. The percutaneous probe can move to the first deployed position when the pre-adjustable portion is in the first position, and can move to the second deployed position when the pre-adjustable portion is in the second position.

In other aspects of the invention, the apparatus can have other arrangements. For example, in one arrangement, at least part of the percutaneous probe can have a generally non-linear shape when the percutaneous probe is in the stowed position, and have a generally linear shape when the percutaneous probe is in a deployed position. In another aspect of the invention, the housing can include multiple percutaneous probes, with different percutaneous probes having different percutaneous lengths. In still a further aspect of the invention, the apparatus can include a tool with an engaging portion positioned to selectively engage the percutaneous probe at first and second axial locations to selectively move the percutaneous probe to corresponding first and second deployed positions. In still a further aspect of the invention, the housing can include an exit portion where the percutaneous probe exits the housing, and an at least partially light transmissive portion to allow visual access to the exit portion. In yet another aspect of the invention, the housing can include a plunger coupled to the percutaneous probe for deploying the percutaneous probe, and an electrical coupling releaseably contacting the percutaneous probe and removable from the housing independently of the plunger.

The invention is also directed to methods for operating percutaneous probes. A method in accordance with one aspect of the invention includes choosing a selected deployment depth from at least a first deployment depth and a second deployment depth, deploying the percutaneous probe in a recipient's tissue to the selected deployment depth, halting deployment of the percutaneous probe at the selected deployment depth with a depth control device having one of at least two configurations, withdrawing the percutaneous probe from the recipient's tissue, and stowing the percutaneous probe in the housing. Methods in accordance with other aspects of the invention include stowing the percutaneous probe in a housing with at least part of the percutaneous probe having a generally non-linear shape, and deploying the percutaneous probe into a recipient's tissue with at least part of the percutaneous probe having a generally linear shape. Another method in accordance with another aspect of the invention includes selecting a percutaneous probe from multiple percutaneous probes in a housing, with different percutaneous probes having different percutaneous lengths.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views. FIGS. 1A-G are schematic illustrations of a percutaneous electrical therapy system according to one embodiment of this invention.

FIG. 1A shows electrode and sharp point protection assemblies wherein the electrode is in an undeployed and uninserted state in accordance with an embodiment of the invention.

FIG. 1B shows the electrode and sharp point protection assemblies of FIG. 1A during deployment but prior to insertion of the electrode into a patient's tissue.

FIG. 1C shows the electrode and sharp point protection assemblies of FIG. 1A during deployment and insertion of the electrode into the patient's tissue.

FIG. 1D shows the electrode of FIG. 1A inserted into the patient's tissue.

FIG. 1E shows the electrode of FIG. 1A attached to a control unit to provide percutaneous electrical therapy.

FIG. 1F shows the electrode and sharp point protection assemblies of FIG. 1A during undeployment but prior to removing the sharp point of the electrode from the patient's tissue.

FIG. 1G shows the electrode and sharp point protection assemblies of FIG. 1A during undeployment and after removing the sharp point of the electrode from the patient's tissue.

FIG. 2A shows a percutaneous electrical therapy system with electrode and sharp point protection assemblies wherein the electrode is in an undeployed and uninserted state.

FIG. 2B shows the percutaneous electrical therapy system of FIG. 2A during deployment, but prior to insertion, of the electrode.

FIG. 2C shows the percutaneous electrical therapy system of FIG. 2A with the electrode in a deployed and inserted state.

FIG. 2D shows the percutaneous electrical therapy system of FIG. 2A during undeployment of the electrode.

FIG. 2E shows the percutaneous electrical therapy system of FIG. 2A after the electrode has been undeployed.

FIG. 4 is an exploded sectional view of an electrode and sharp point protection assembly according to yet another embodiment of the invention.

FIG. 5 is a partially exploded elevational view of the embodiment of FIG. 4.

FIG. 6 is an elevational view of the embodiment of FIG. 4 showing the electrode and sharp point protection assemblies and an actuator tool.

FIG. 7 is a sectional view of the embodiment of FIG. 4 showing the electrode and sharp point protection assemblies and an actuator tool.

FIG. 8 is a sectional view of the embodiment of FIG. 4 showing the actuator tool in engagement with the electrode and sharp point protection assemblies prior to insertion of the electrode into a patient's tissue.

FIG. 9 is a sectional view of the embodiment of FIG. 4 with the electrode in its deployed and inserted state.

FIGS. 29A-29B illustrate a percutaneous apparatus configured in accordance with another embodiment of the invention.

FIG. 29C illustrates a portion of the apparatus shown in FIGS. 29A-29B.

FIGS. 35A-39B illustrate percutaneous apparatuses having actuator tools in accordance with still further embodiments of the invention.

DETAILED DESCRIPTION

Figure 2A:
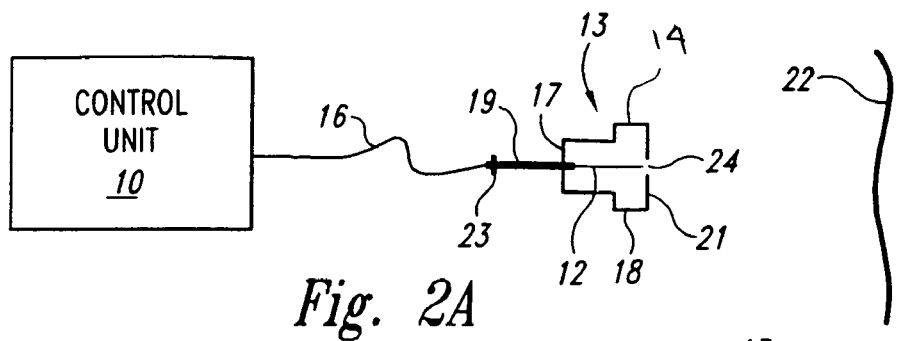
FIGS. 2A-E are schematic renderings of a percutaneous electrical therapy system according to another embodiment of the invention.

Percutaneous electrical therapy systems, such as PNT systems, deliver electric current to a region of a patient's tissue through electrodes that pierce the skin covering the tissue. The electric current is generated by a control unit external to the patient and typically has particular waveform characteristics such as frequency, amplitude and pulse width. Depending on the treatment or therapy being delivered, there may be one electrode containing both a cathode and an anode or a plurality of electrodes with at least one serving as a cathode and at least one serving as an anode.

The electrode has a sharp point to facilitate insertion through the patient's skin and to enhance local current density during treatment. Once inserted into the skin, the sharp point may become exposed to pathogens, microbes, toxins, etc., in the patient's tissue and/or blood. After removal of the electrode from the patient's tissue, a caregiver or other bystander may be stuck accidentally with the sharp point of the electrode, thereby exposing the caregiver to any pathogens that may be on the used electrode. This invention therefore includes a sharp point protection assembly for a percutaneous electrical therapy system.

FIGS. 1A-G are block diagrams showing deployment and use of one embodiment of the percutaneous electrical therapy system and electrode assembly invention. As shown in FIGS. 1A and 1B, the system can include a sharp probe, such as an electrode 1 having a sharp point 2 at its distal end and a sharp point protection assembly 3 surrounding at least the electrode's sharp point 2 when the electrode is in its undeployed and uninserted states. The undeployed and uninserted states include pre-deployment and post-deployment states of the electrode. In this embodiment, the sharp point protection assembly 3 includes a housing 4 with an aperture 5 at its distal end. An actuator 6 interacts with a handle 11 at the proximal end of the electrode 2 as shown.

Deployment of the electrode assembly includes the steps taken to place the electrode assembly in proper position and condition for use in electrical therapy. FIG. 1A shows the electrode assembly in an undeployed (pre-deployed) state. During deployment, the aperture 5 is placed against a patient's skin 22, as shown in FIG. 1B. The electrode 2 is then inserted into the tissue underlying the patient's skin by moving actuator 6 distally, as shown in FIG. 1C. The actuator 6 may have an optional limit stop element 9 cooperating with a limit stop area 8 of the housing 4 to limit distal motion of the actuator 6 and to control the depth of insertion of the sharp point 2 of electrode 1. In a preferred embodiment of the invention, for example, where the electrical therapy system is used to provide percutaneous neuromodulation therapy, the predetermined electrode depth is 3 cm. Other electrode depths may be used, of course, depending on the intended application and therapy.

After insertion, the housing 4 and actuator 6 (which have heretofore acted as an electrode introducer) are preferably removed, as shown in FIG. 1D. Electrode 1 is connected to a control unit 10 via a conductor or cable 16. For use with PNT, control unit 10 preferably supplies a current-regulated and current-balanced waveform with an amplitude of up to approximately 20 mA, frequency between approximately 4 Hz and 50 Hz, and pulse width of between approximately 50 µsec and 1 msec. Other electrical waveforms having other parameters may be used, of course, depending on the therapy to be provided. Examples of electrical signals having other characteristics are included in the following pending U.S. patent applications Ser. No. 09/686,993, filed Oct. 10, 2000; and Ser. No. 09/751,503, filed Dec. 29, 2000, both of which are incorporated herein in their entireties by reference. In still further embodiments, the control unit 10 can be configured to receive and/or transmit diagnostic signals in addition to or in lieu of therapeutic signals. Also, while FIG. 1E shows only one electrode connected to the control unit, it should be understood that a plurality of electrodes may be connected to a single control unit, as called for by the desired electrical stimulation treatment.

After completion of electrical therapy, the electrode assembly is undeployed. During undeployment, the electrode must be removed from the patient in a sharps-safe manner. In this embodiment, as shown in FIG. 1F, the aperture 5 of the housing 4 of a sharp point protection assembly 3 is placed over the handle portion 11 of electrode 1. Sharp point protection assembly 3 may be the same assembly used to deploy and insert the electrode (i.e., the electrode introducer), or it may be an entirely different assembly (e.g., an electrode remover). The sharp point 2 of electrode 1 is then drawn into housing 4 of sharp point protection assembly 3 by moving actuator 6 proximally, as shown in FIG. 1G. Thus, sharp point protection assembly 3 of FIGS. 1A-G helps prevent all unintended contact between the electrode's sharp point and a caregiver or other bystander before, during and after deployment of the electrode.

FIGS. 2A-E are block diagrams of another embodiment of our percutaneous electrical therapy system and electrode assembly invention. A control unit 10 is connected to an electrode 12 within an electrode assembly 13 via a conductor 16. As above, for use with PNT, control unit 10 preferably supplies a current-regulated and current-balanced waveform with an amplitude of up to approximately 20 mA, frequency between approximately 4 Hz and 50 Hz, and pulse width of between approximately 50 µsec and 1 msec. As shown in its undeployed state in FIG. 2A and in its uninserted state in FIG. 2B, the system includes a sharp point protection assembly 14 comprising a housing 18 surrounding the sharp point 20 of an electrode 12 when the electrode point 20 has not yet been inserted through the patient's skin 22.

Figure 2B:
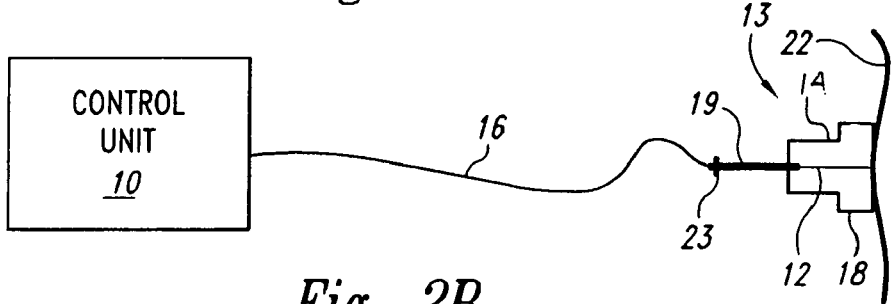
Figure 2C:
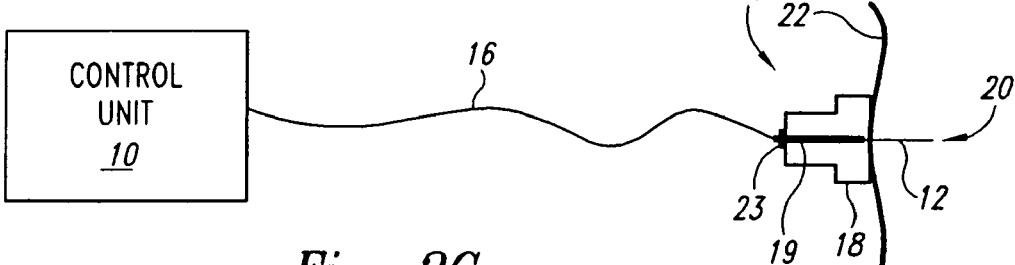

To begin deployment, a distal face 21 of housing 18 is placed against the patient's skin 22, as shown in FIG. 2B. The system may also include an electrode actuator 19 that enables deployment and insertion of the sharp point 20 of the electrode 12 through the patient's skin 22 into the underlying tissue to a predetermined depth through an aperture 24 in the housing 18, as shown in FIG. 2C. An actuator 19 may be part of the electrode assembly 13 or a separate component of the system. The actuator 19 may have an optional limit stop element 23 that cooperates with a limit stop area 17 of the housing 18 to limit distal movement of the actuator 19, thereby controlling depth of insertion of the electrode 12. In a preferred embodiment of the invention, for example, where the electrical stimulation system is used to provide percutaneous neuromodulation therapy, the predetermined electrode depth is approximately 3 cm., although other electrode depths may be used depending on the application. The control unit 10 may provide the appropriate therapy to the patient through the electrode 12 and any other electrodes connected to it.

Figure 2D:
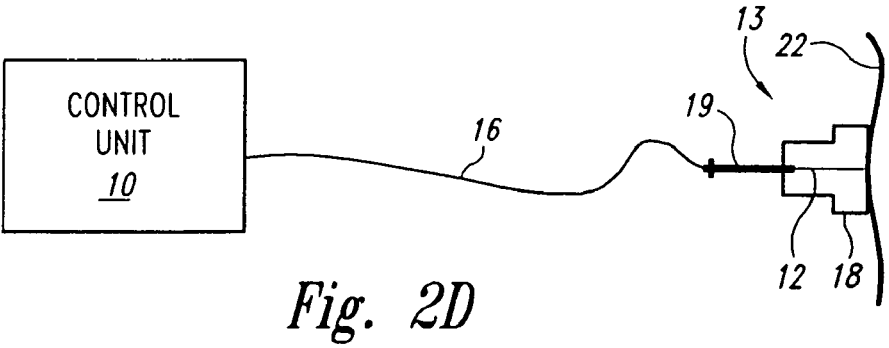
Figure 2E:
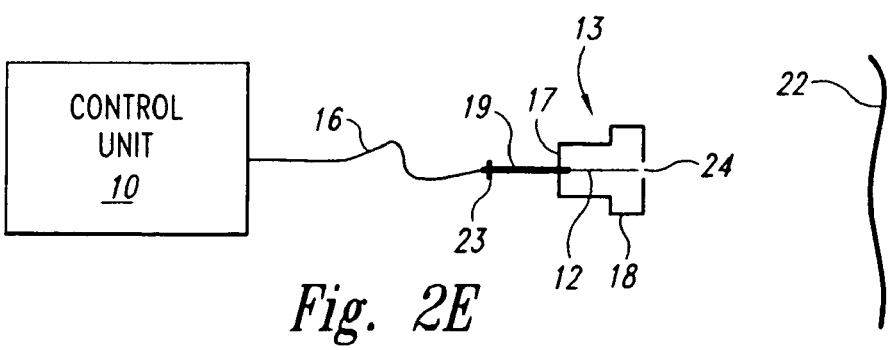

During undeployment, the actuator 19 is used to draw the electrode 12 back proximally into the housing 18. After removal of the electrode 12 from the patient's skin, the housing 18 of the sharp point protection assembly 14 once again surrounds the sharp point 20 of the now uninserted electrode 12, as shown in FIGS. 2D and 2E. The actuator 19 helps to enable this operation to occur without ever exposing the sharp point of the electrode 12 when the sharp point is no longer in the patient. In fact, the operator of the electrode assembly never sees the sharp point of the electrode 12. Thus, the sharp point protection assembly 14 shields the potentially contaminated portion of the undeployed electrode 12 and protects the patient's caregiver or other bystander from unintended contact with the sharp point of the electrode 12 before, during and after electrical therapy.

While FIGS. 2A-E show the electrode connected to the control unit prior to deployment and insertion of the electrode into the patient's skin, the connection between the control unit and the electrode could be made during deployment or after insertion. Also, while FIGS. 2A-E show only one electrode connected to the control unit, it should be understood that a plurality of electrodes may be connected to a single control unit, as called for by the desired electrical stimulation treatment.

Figure 3:
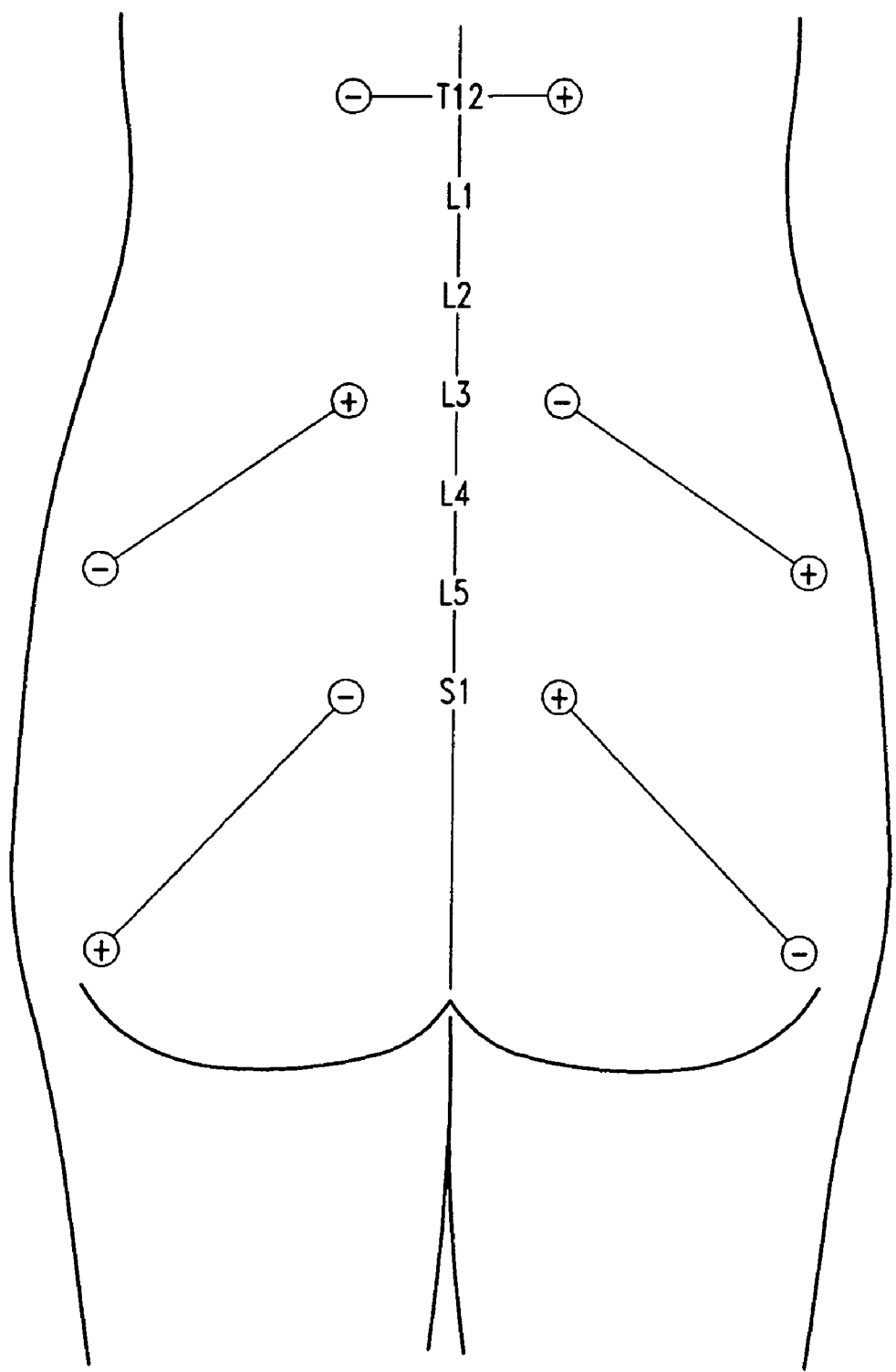
FIG. 3 shows an electrode montage for use in percutaneous neuromodulation therapy to treat low back pain.

To use the percutaneous electrical therapy systems of FIGS. 1A-G and FIGS. 2A-E to treat a patient, one or more electrodes are inserted through the patient's skin into the underlying tissue. As an example, to treat low back pain using PNT with unipolar electrodes, an array or montage such as that shown in FIG. 3 may be used. The "T12" -"S1" designations refer to the patient's vertebrae. The sharp point protection assembly shields the electrode assembly operator from exposure to the electrode's sharp point prior to, during and after treatment. The control unit or generator supplies current pulses between pairs of electrodes for durations of a few minutes to several hours, preferably delivering the current-regulated waveform described above. Thirty-minute treatments are recommended in the Ghoname et al. low back pain treatment articles.

During deployment and treatment, the electrode assembly and other parts of the system perform other functions in addition to being a sharps-protected conduit for current flow into the patient. For example, in the embodiment of FIGS. 2A-E, the aperture 24, the distal face 21 and the interaction of the actuator 19 and the housing 18 cooperate as an electrode angle of entry controller to control the electrode's entry angle during insertion of the sharp point of the electrode into the patient's tissue. The interaction of the aperture 5, the distal face 7 of the housing 4, and the interaction of the actuator 6 and the housing 4 perform this function in the embodiment of FIGS. 1A-G.

Additional optional details of the electrode assembly may be found in the following concurrently filed and commonly owned U.S. patent applications, the disclosures of which are incorporated herein by reference: Bishay et al., "Percutaneous Electrical Therapy System With Electrode Entry Angle Control;" Leonard et al., "Percutaneous Electrical Therapy System Providing Electrode Axial Support;" Leonard et al., "Percutaneous Electrical Therapy System With Electrode Depth Control;" Leonard et al., "Percutaneous Electrical Therapy System With Electrode Position Maintenance;" Leonard et al., "Electrode Introducer For A Percutaneous Electrical Therapy System;" Bishay et al., "Percutaneous Electrical Therapy System For Minimizing Electrode Insertion Discomfort;" Bishay et al., "Electrode Assembly For A Percutaneous Electrical Therapy System;" and Leonard et al., "Electrode Remover For A Percutaneous Electrical Therapy System."

FIGS. 4-12 show another embodiment of the invention. An electrode assembly 30 includes a base 32, an electrode 34, and a plunger or actuator 36. The base 32 has a flange or flared end 44 that is adapted to make contact with a patient's skin. The base 32 may be formed from any suitable polymer or metal, such as a high density polyethylene (HDPE). The base 32 is preferably opaque so that the electrode cannot be seen by a 'needle-shy' patient.

An actuator 36 fits within a housing portion 40 of the base 32 in a slidable arrangement. A locking assembly is operable to prevent relative movement between the actuator 36 and the housing 40 of the base 32. In this embodiment, the locking assembly of the actuator 36 has integrally-formed resilient detents 48 on its exterior cylindrical surface. In the undeployed state of an electrode assembly 30, the detents 48 mate with corresponding openings 50 in the base 32 to hold the actuator 36 and the base 32 in place with respect to each other to prevent an electrode 34 from moving outside of the protective housing 40 of the base 32 and thereby providing sharp point protection, as explained further below. Mechanisms other than the detent and opening arrangement shown here may be used to hold the actuator and base in place without departing from the invention.

In this embodiment, the electrode 34 is preferably a 3 cm. long 32 gauge stainless steel needle. Other sizes and materials may be used for the electrode 34, of course, without departing from the scope of the invention. The actuator 36 is preferably formed from HDPE as well, although other suitable materials may be used.

The electrode 34 has a larger-diameter handle 52 at its proximal end. The handle 52 fits within a channel 54 formed within the actuator 36. A channel 54 has a narrow opening 56 at its distal end whose diameter is slightly larger than the diameter of the electrode 34 but narrower than the diameter of the handle 52 to hold the electrode 34 in place within the actuator 36 after initial manufacture and assembly. As shown in FIG. 7, in an undeployed state the sharp point 38 of the electrode 34 is disposed within the housing portion 40 of the base 32, specifically, within a narrow channel 42 of the housing 40.

To deploy one or more electrode assemblies on a patient in order to provide electrical stimulation therapy (such as PNT), the distal surface 46 of a flange portion 44 of the base 32 is mounted on the desired site on the patient's skin, preferably with a compressible adhesive pad (not shown) surrounding a ring 43 extending downward from a surface 46 around an aperture 41 formed at the distal end of the channel 42, although other means of attaching the base 32 to the patient may be used as appropriate.

An electrical connector and actuator tool 60 is used to insert the electrode and connect the electrode electrically with a control unit 62. The actuator tool 60 and the electrode assembly 30 also interact to provide the sharp point protection assembly of this embodiment. When the distal end of the actuator tool 60 is placed against the proximal ends of the base 32 and the actuator 36, the exposed proximal end 64 of the electrode handle 52 makes electrical contact with a contact surface 66 within actuator tool 60. A contact surface 66, in turn, is electrically connected to the control unit 62 via a cable or other conductor 68.

The actuator tool 60 has two oppositely disposed pegs 70 extending outward from the distal portion of its cylindrically surface. The pegs 70 mate with two corresponding slots 72 in the actuator 36 and with two corresponding grooves 74 in the base 32. (The second slot 72 and second groove 74 are each opposite the slot 72 and the groove 74, respectively, shown in FIGS. 4 and 5.) When connecting the actuator tool 60 to the electrode assembly 30, the pegs 70 move along longitudinal portions 76 of the slots 72 and along longitudinal portions 78 of the grooves 74. Concurrently, the exposed distal end 64 of the electrode handle 52 begins to make sliding contact with the contact surface 66 of the actuator tool 60 to create the electrical connection between the actuator tool 60 and the electrode 32.

Clockwise rotation (looking down on the assembly) of the actuator tool 60 after the pegs 70 reach the end of the longitudinal portions 76 and 78 moves the pegs 70 into short circumferential portions 80 and 82, respectively, of the slots 72 and the grooves 74. The length of the circumferential portions 80 of the slots 72 is less than the length of the circumferential portions 82 of the grooves 74. Continued movement of the pegs 70 along the circumferential portions 82 will therefore move the pegs 70 against the ends 81 of the circumferential portion 80. Further clockwise rotation of the actuator tool 60 will cause the actuator 36 to rotate clockwise as well, thereby moving the detents 48 out of the openings 50 and allowing the electrode 34 and the actuator 36 to move with respect to the base 32.

Second longitudinal portions 84 of the grooves 74 are formed in the base 32 at the end of the circumferential portions 82. Movement of the pegs 70 distally along the longitudinal portions 84 pushes the pegs 70 against the distal edges of the circumferential slot portions 80, thereby moving the actuator 36 and the electrode 34 distally toward the patient's skin 22.

In one aspect of this embodiment, the housing 40 can include a depth control device 480 configured to control the depth to which the electrode 34 deploys into the patient's skin. In one aspect of this embodiment, the depth control device 480 can include one or more breakaway tabs 482 (one is shown in FIG. 4) axially spaced apart along the longitudinal portion 84 of the groove 74. Each breakaway tab 482 can have a contact portion 484 that extends into the longitudinal portion 84 to block further downward movement of the actuator 36. Accordingly, when the breakaway tab 482 is positioned in the housing 40, it can limit the depth to which the electrode 34 deploys. When the breakaway tab 482 is removed, the actuator 36 can continue downwardly to the next breakaway tab (if the housing 40 includes more than one breakaway tab 482), or the actuator 36 can continue downwardly to its lowest position (if the housing 40 includes no further breakaway tabs 482). The breakaway tab 482 can include a projection 486 (FIG. 6) extending outwardly from the housing 40, which allows the practitioner to grasp and remove the breakaway tab 482 if desired. In other embodiments, the housing 40 can include other depth control devices, such as those described below with reference to FIGS. 29-34.

Upon movement, electrode 34 passes through channel 42, and the sharp point of the electrode 34 moves out through the aperture 41. The channel 42 and the actuator 36 provide axial support to the electrode 34 during this forward movement and also, along with the support provided by the flange 44, provide entry angle guidance to the electrode. In addition, downward pressure on the patient's skin during electrode deployment compresses the compressible adhesive pad and presses a ring 43 against the patient's skin 22, which helps ease electrode entry through the skin and also lessens the insertion pain experienced by the patient.

If the housing 40 does not include breakaway tabs 482 (or if all the breakaway tabs 482 have been removed), distal movement of the electrode and its actuator within the base 32 continues until the distal surface 86 of a cylindrical cap portion 92 of the actuator tool 60 meets an annular surface 88 of the housing 40. At this point, the sharp point 38 of the electrode 34 has extended a predetermined depth into the tissue underlying the patient's skin. In the preferred embodiment, this predetermined depth is approximately 3 cm., although other electrode depths may be desired depending on the treatment to be performed.

An optional feature of the invention is a deployed electrode holding mechanism. In that embodiment, an interference fit between the inner surface of the channel 42 and the outer surface (not shown) of channel 52 performs this function.

Electrical stimulation treatment may begin once the electrodes have been deployed and inserted. Control unit 62 supplies a stimulation current to the electrodes, e.g., in the manner described in the Ghoname et al. articles. The electrical waveform provided by the control unit depends on the application. For example, in an embodiment of a system providing percutaneous neuromodulation therapy, the control unit 62 would preferably provide a current-regulated and current-balanced waveform with an amplitude of up to approximately 20 mA, frequency between approximately 4 Hz and 50 Hz, and pulse width of between approximately 50 µsec and 1 msec.

The interaction of the actuator tool 60 and the base 32 provides stability to the electrode 34 and its electrical connection to the control unit 62 during treatment by holding the electrode 34 in place, by providing strain relief for tugging forces on the conductor 68, and by providing a robust mechanical connection. It should be noted that the sharp point of the electrode is not exposed to the operator or to any other bystander at any point during deployment and use of the electrode 34 assembly.

After treatment has been completed, the electrode 34 may be removed from the patient. To do so, the actuator tool 60 is moved proximally away from the patient. As the pegs 70 move proximally along the longitudinal portions 84 of the grooves 74, the pegs 70 push against proximal edges of the actuator's circumferential slot portions 80, thereby moving the actuator 36 and the electrode 34 proximally as well. When the pegs 70 reach the proximal end of the longitudinal groove portions 84, the sharp end 38 of the electrode 34 is out of the patient and safely inside the housing 40 of the base 32. Counterclockwise movement of the actuator tool 60 moves the pegs 70 along the circumferential portions 80 and 82 of the slot 72 and the groove 74, respectively. Since, as discussed above, the circumferential portion 80 is shorter than the circumferential portion 82, this counterclockwise movement will turn the actuator 36 counterclockwise.

At the limit of the counterclockwise movement, the detents 48 move back into the openings 50 to prevent further movement of the electrode 34 and the actuator 36 with respect to the base 32. Further distal movement of the actuator tool 60 moves the pegs 70 distally along the longitudinal portions 76 and 78 of the slot 72 and the groove 74, respectively, to disconnect the actuator tool 60 from the electrode assembly 30. The base 32 can then be removed from the patient.

Once again, at no time during the electrode deployment, use or removal processes was the sharp point of the electrode exposed to the operator or bystanders.

Figure 10:
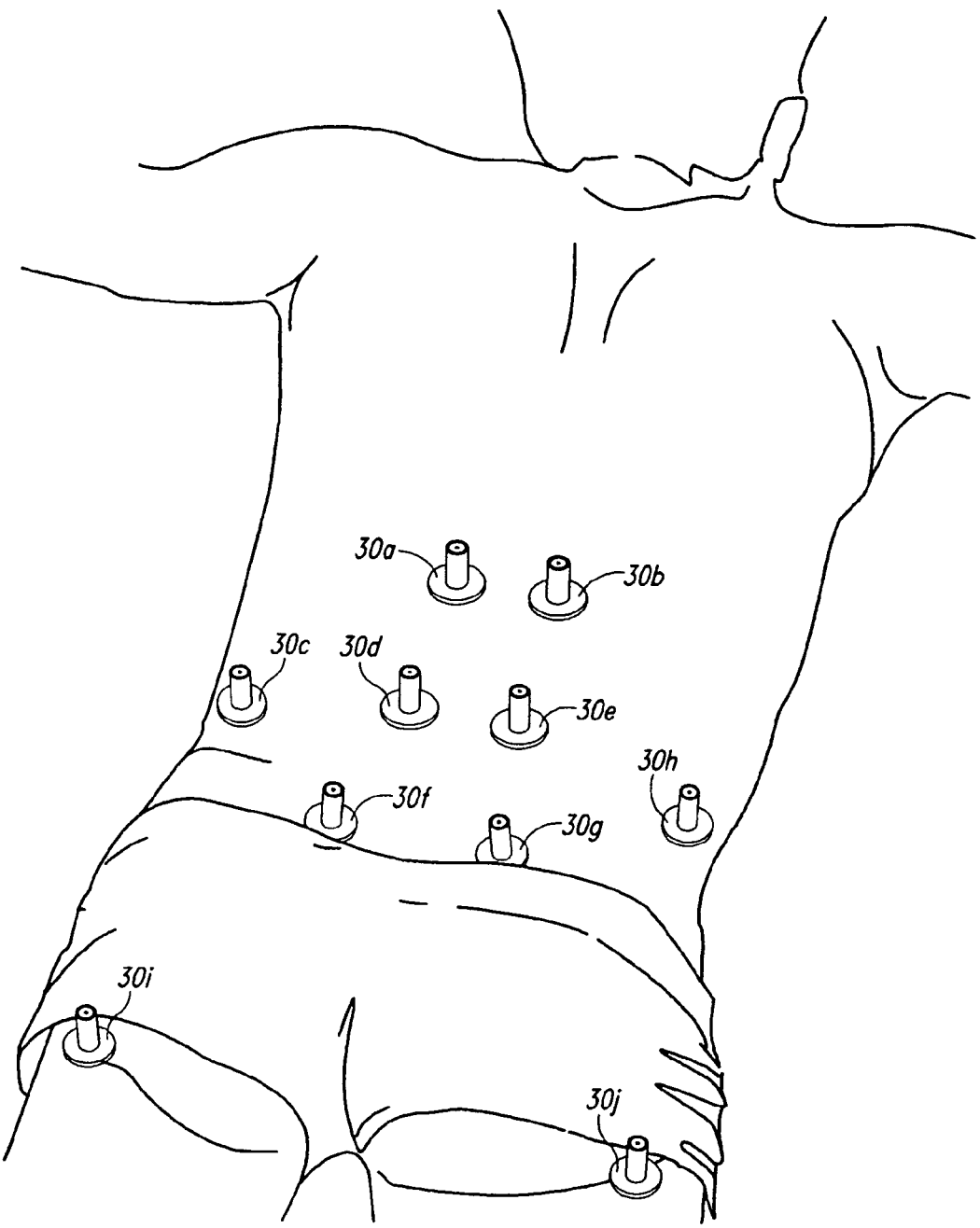
FIG. 10 shows a montage for using the embodiment of FIG. 4 to treat low back pain with the electrodes in a partially deployed but uninserted state.
Figure 11:
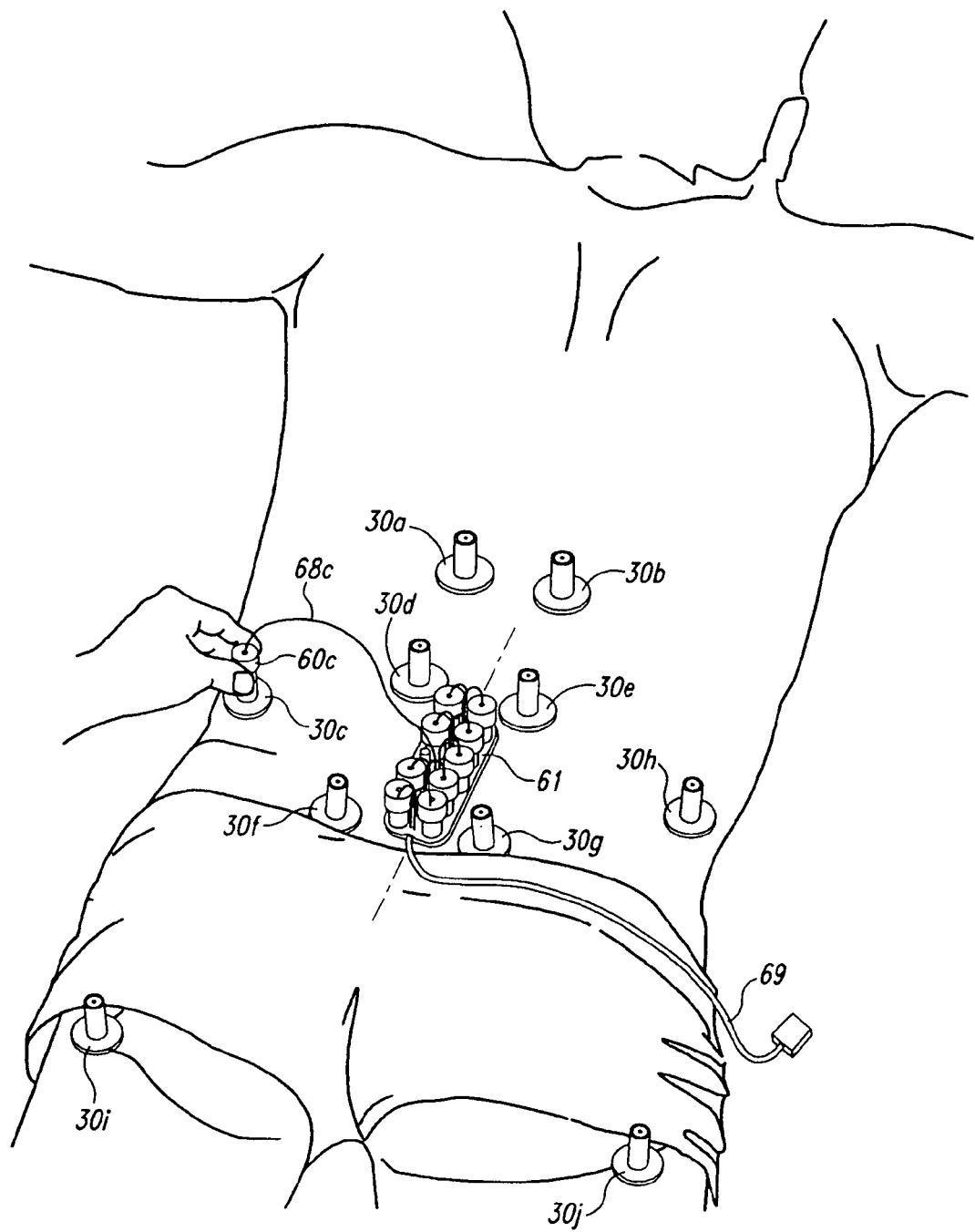
FIG. 11 shows the electrode montage of FIG. 10 at the beginning of the electrode insertion step.
Figure 12:
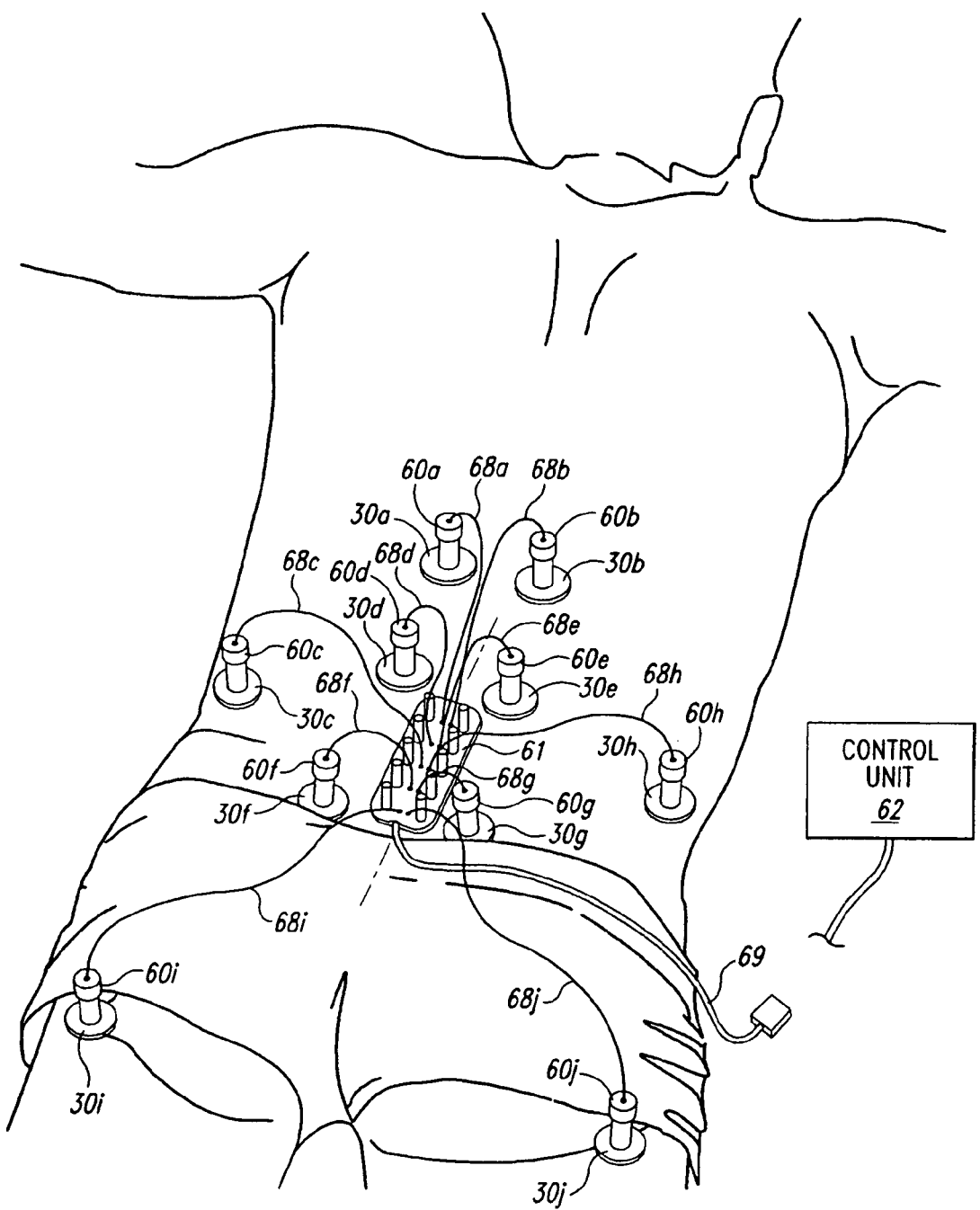
FIG. 12 shows the electrode montage of FIG. 10 with the electrodes deployed, inserted and attached to a control unit to provide electrical therapy to the patient.

FIGS. 10-12 show the use of the electrode and the sharp point protection assemblies of FIGS. 4-9 to treat low back pain using PNT. As shown in FIG. 10, ten electrode assemblies 30*a-j* are arranged in a montage on the patient's back and attached with adhesive. Next, ten actuator tools 60*a-j* are attached to the ten electrode assemblies 30*a-j*. In this example, prior to deployment the actuator tools are mounted on an actuator tool tray 61 that provides electrical communication to a control unit 62 via a cable 69. The actuator tools electrically connect with the tool tray 61, and thereby to the cable 69 and the control unit 62, via individual cables 68*a-j*. It should be understood that the tool tray 61 and its electrical connection scheme play no part in the invention. FIG. 11 shows the beginning of the electrode insertion process.

Once each electrode assembly has been actuated by its respective actuator tool to insert an electrode into the patient's tissue (as shown in FIG. 12), the control unit 62 provides electrical signals to treat the patient. Preferably, half the electrodes (e.g., assemblies 30*b*, 30*d*, 30*g*, 30*h* and 30*i*) are treated as anodes, and the other half as cathodes. In the preferred embodiment, the control unit 62 would provide a current-regulated and current-balanced waveform with an amplitude of up to approximately 20 mA, frequency between approximately 4 Hz and 50 Hz, and pulse width of between approximately 50 μsec and 1 msec. to treat the patient's low back pain using PNT.

Another embodiment of the invention is shown in FIGS. 13-28. In this embodiment, an electrode introducer and an electrode remover cooperate to provide sharp point protection.

In one embodiment, an electrode introducer 100 shown in FIGS. 13-16 and 19-21 is designed to insert multiple electrodes or other percutaneous probes. It should be understood that the principles of this invention could be applied to an introducer designed to hold and insert any number of electrodes.

Twelve electrodes 102 are disposed within a magazine 103 rotatably mounted within a housing 104. In this embodiment, the housing 104 is a two-part injection molded polystyrene assembly. As seen best in FIG. 14, the magazine 103 rotates about a hub 105 mounted on supports formed in the housing 104. A leaf spring 106 mates with one of twelve radial grooves 108 formed in the magazine 103 to form a twelve-position ratchet mechanism for rotatable magazine 103 in the housing 104.

Figure 14:
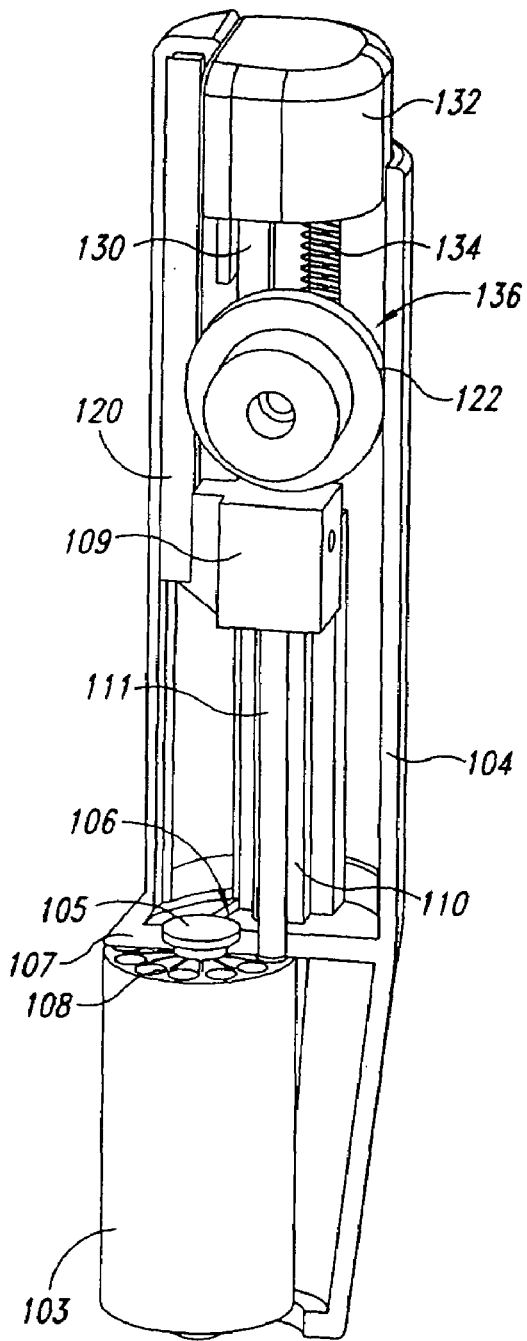
FIG. 14 is a partial sectional view of the introducer and sharp point protection assembly of FIG. 13.
Figure 15:
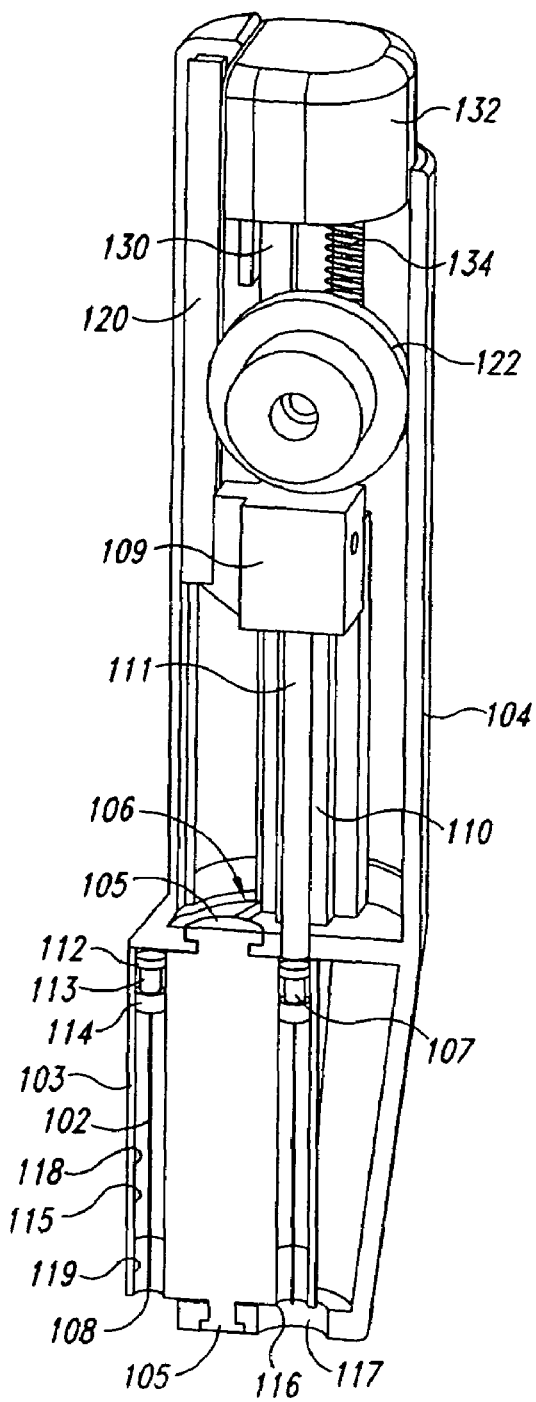
FIG. 15 is a sectional view of the introducer and sharp point protection assembly of FIG. 13.
Figure 16:
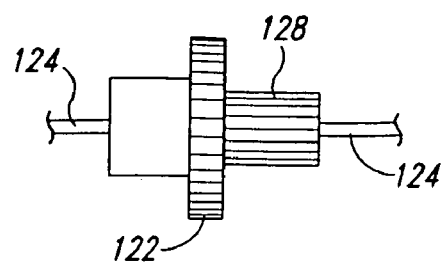
FIG. 16 is an elevational view of gear assemblies of the introducer and sharp point protection assembly of FIG. 13.

The magazine 103 has twelve electrode chambers 115 arranged radially about hub the 105. When the introducer 100 is completely full, each chamber 115 contains one electrode 102. The diameter of an upper portion 118 of the chamber 115 is sized to form an interference fit with wider portions 112 and 114 of an electrode handle portion 107 of the electrode 102. The lower wide portion 114 of the electrode 102 is formed from a compressible material. The diameter of a lower portion 119 of the chamber 115 is slightly larger so that there is no interference fit between the chamber portion 119 and the electrode handle 107, for reasons explained below. Each time the leaf spring 106 is within a groove 108, the opening 106 of a magazine chamber 115 is lined up with the aperture 117 of the introducer 100, as shown in FIGS. 14 and 15.

A slide member 109 is disposed on a rail 110 formed in the housing 104. Extending longitudinally downward from the slide member 109 is a drive rod 111, and extending longitudinally upward from the slide member 109 is a gear rack 120. The teeth of the gear rack 120 cooperate with teeth on a rotational gear 122 mounted about a shaft 124 extending into a shaft mount 126 formed in the housing 104. A second set of teeth are mounted on a smaller diameter rotational gear 128 (shown more clearly in FIG. 16) which is also mounted about the shaft 124. The gears 122 and 128 rotate together about the shaft 124.

The teeth of a smaller diameter gear 128 mesh with the teeth of a second gear rack 130 extending from a longitudinally-movable actuator 132. A spring 134 mounted between the actuator 132 and a spring platform 136 biases the actuator 132 away from the housing 104.

To deploy the electrode assembly of this embodiment, a flexible and compressible annular patch 140 is placed on the patient's skin at the desired site, preferably with adhesive (not shown). For example, to treat low back pain using PNT, the arrangement or montage shown in FIG. 17 may be used. In this montage, five electrodes serve as cathodes and five serve as anodes.

Figure 20:
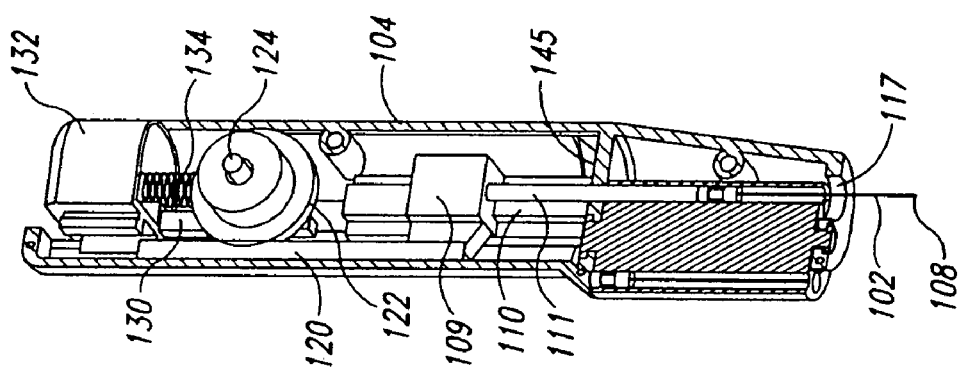
FIG. 20 is a sectional view showing the introducer of FIG. 13 in the process of deploying an electrode, during insertion of the electrode.
Figure 19:
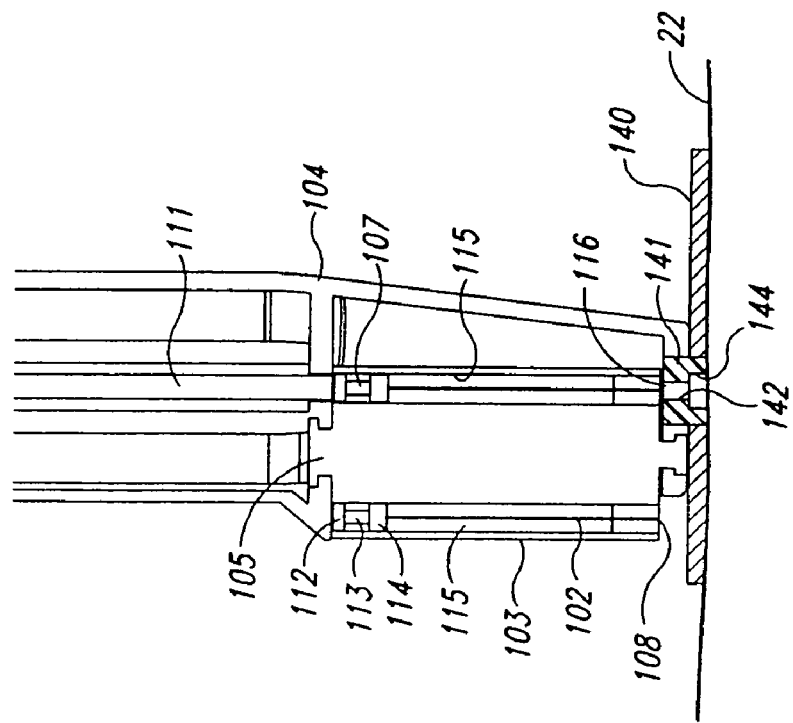
FIG. 19 is a sectional view showing the introducer of FIG. 13 in the process of deploying an electrode, prior to insertion of the electrode.

As shown in FIGS. 19 and 20, the patch 140 has an annular rigid member 141 disposed in its center and extending upwardly from it. The rigid member 141 has a smaller diameter opening 142 leading to a larger diameter opening 144. The diameter of the opening 142 is slightly smaller than the lower wide portion 114 of the handle portion 107 of the electrode 102 and slightly larger than the diameter of the central portion 113 of the handle portion 107 of the electrode 102.

Figure 18:
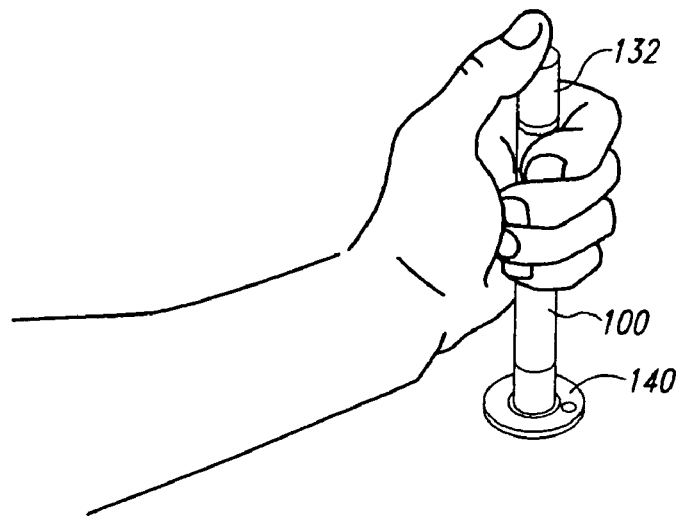
FIG. 18 is an elevational view showing the introducer of FIG. 13 in the process of deploying an electrode.

After the patch 140 is in place, the distal end of the introducer 100 is placed against the patch 140 so that the introducer aperture 117 surrounds the upwardly extending portion of the rigid patch member 141, as shown in FIG. 18. This interaction aligns the opening 116 of one of the introducer's magazine chambers 115 with the opening 142 of the rigid member 141 and helps control the electrode's angle of entry, as shown in FIG. 19. Downward pressure on the introducer 100 compresses the patch 140, thereby causing the upper surface of the rigid member 141 to engage a lower surface of the magazine 103 and press the rigid member 141 downward into the patient's skin 22. This pressure on the patient's skin around the insertion site minimizes the pain of insertion of the electrode.

Depressing the actuator 132 moves the second gear rack 130 distally, which causes the gears 128 and 122 to rotate. Because of the relative diameters and relative tooth counts of the gears 128 and 122, the gear rack 120 moves longitudinally a much greater distance than the corresponding longitudinal movement of the second gear rack 130. This feature enables the electrode to be inserted a required distance into the patient's skin using only a comparatively small movement of the operator's thumb. Distal movement of the gear rack 120 is guided by the movement of the slide member 109 along the rail 110.

As the slide member 109 moves distally, the drive rod 111 moves into the magazine chamber 115 until the distal end of the drive rod 111 engages the top surface of the electrode's handle portion 107. As shown in FIG. 20, further distal movement of the drive rod 111 pushes the electrode 102 downward so that the sharp point 108 of the electrode 102 leaves the introducer housing and enters the patient's skin 22 and the tissue beneath the skin. The skin chamber 115 provides axial stability to the electrode 102 during insertion.

When the top portion 112 of the electrode handle portion 107 leaves the smaller diameter portion 118 of the magazine chamber 115, it enters the larger diameter portion 119 of the chamber 115. At this point (shown in FIG. 21), because the diameter of the chamber portion 119 is wider than the diameter of the electrode handle 107, the electrode 102 is no longer attached to the introducer 100.

Continued downward movement of the actuator 132 and the drive rod 111 pushes the lower larger diameter portion 114 of the electrode handle 107 through the smaller diameter portion 142 of the rigid member 141 by compressing the handle portion 114. Further downward movement pushes the handle portion 114 into the larger diameter portion 144 of the rigid member 141 so that the rigid member's smaller diameter portion lies between the larger diameter portions 112 and 114 of the electrode handle 107. This interaction holds the electrode 102 in place in the patient's tissue and helps provide depth control for electrode insertion. In this embodiment, the preferred depth of the electrode's sharp point 108 is approximately 3 cm., although other electrode depths may be desired depending on the treatment to be performed. The slide member 109 also acts as a limit stop at this point when engaging a limit stop area 145 of the housing 104, thereby also controlling electrode insertion depth.

Figure 22:
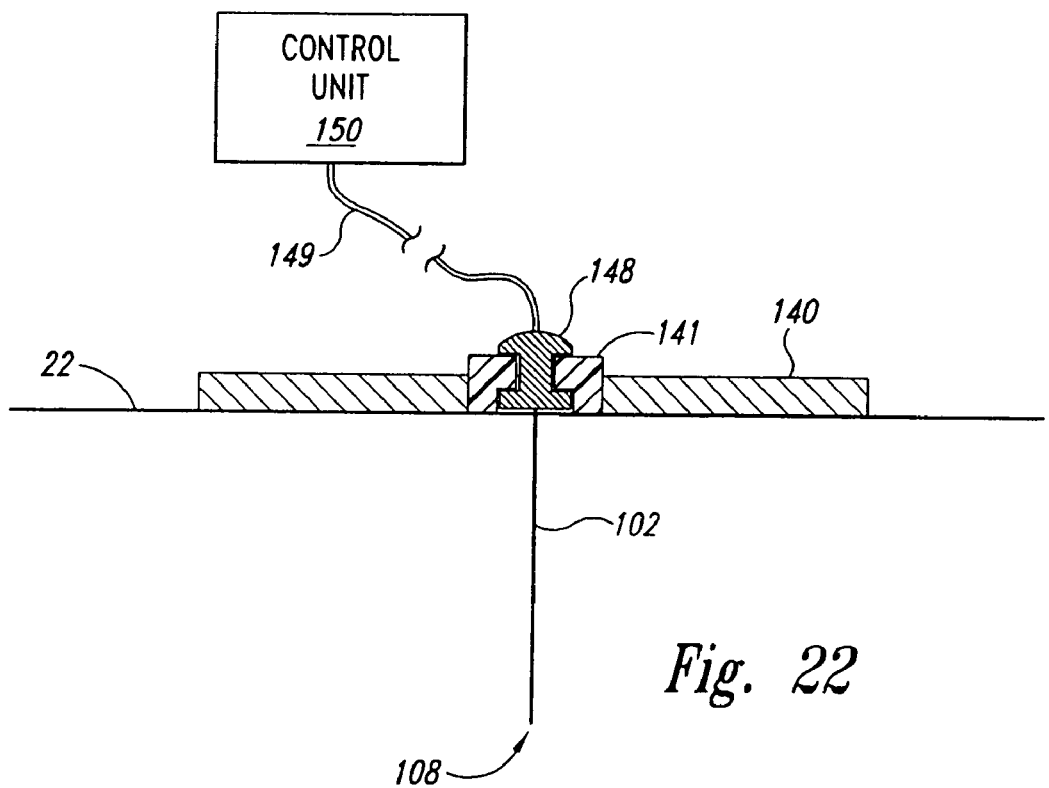
FIG. 22 is a sectional view of an inserted electrode assembly of the embodiment of FIGS. 13-16.
Figure 17:
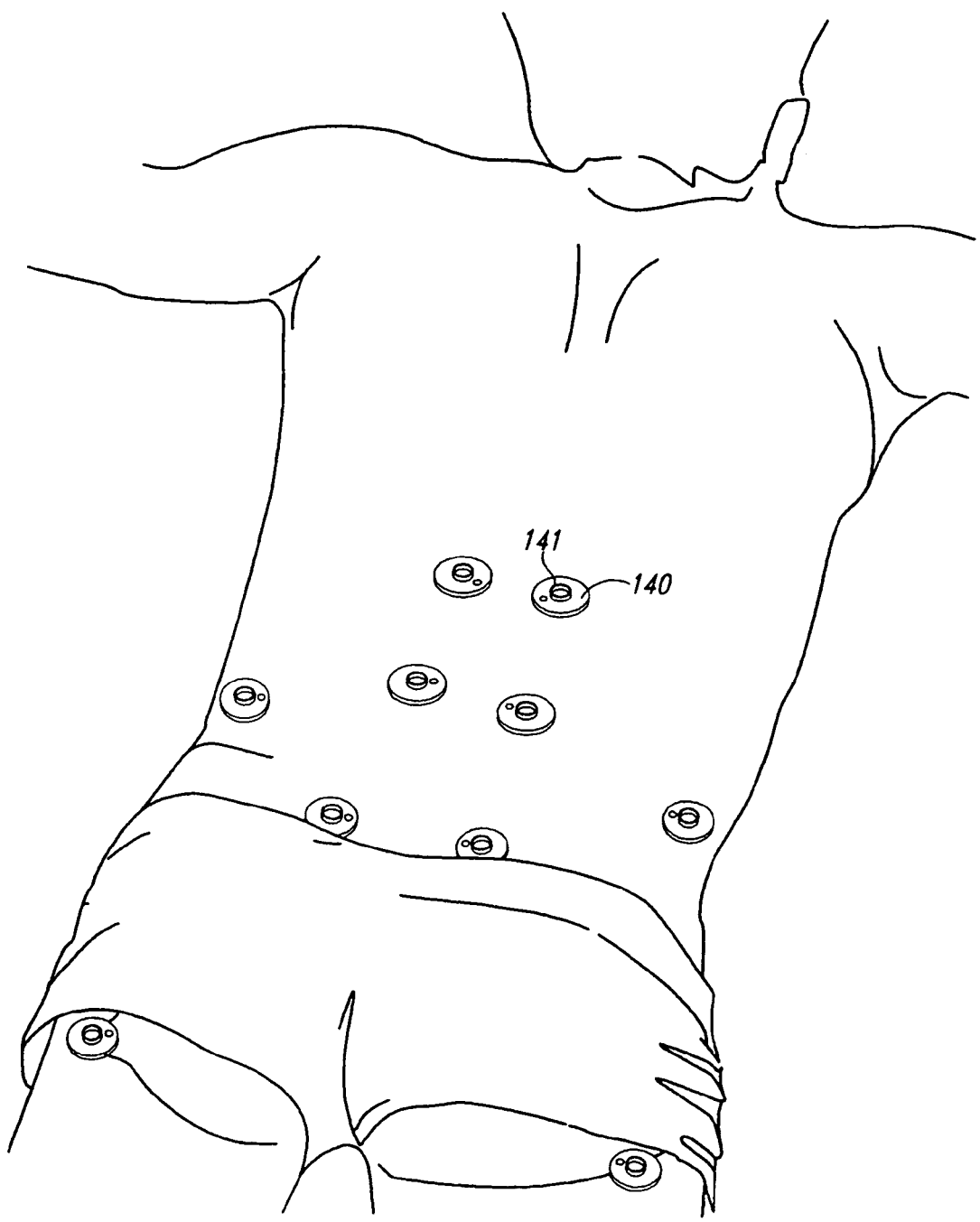
FIG. 17 shows part of the electrode assembly of the embodiment of FIGS. 13-16 in a montage used for treating low back pain using PNT.
Figure 21:
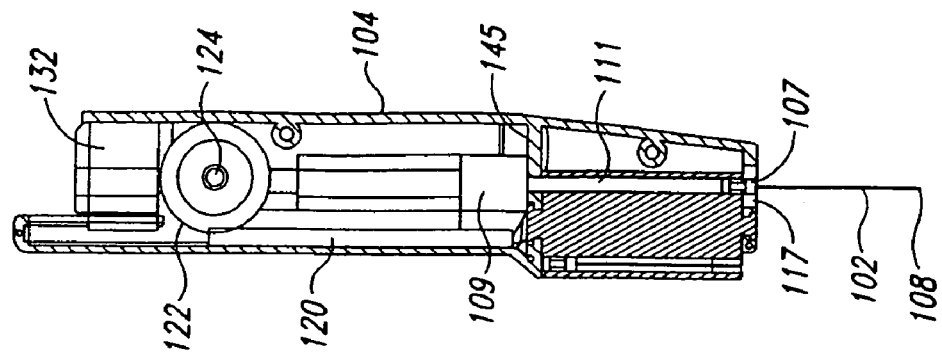
FIG. 21 is a sectional view showing the introducer of FIG. 13 in the process of deploying an electrode, also during insertion of the electrode.

The magazine 103 is rotated to a new insertion position and placed against an empty patch 140 after insertion of each electrode until all electrodes have been deployed and inserted. A suitable electrical connector 148 such as an alligator clip is electrically connected to the electrode 102 through an aperture (not shown) formed in the upper larger diameter portion 112 of the electrode handle 107 to provide electrical communication between a control unit 150 and the electrode 102 via the cable or other conductor 149, as shown in FIG. 22. The patch 140 provides strain relief for the electrode 102 by preventing tugging forces on the cable 149 from dislodging the electrode 102 from the patient, thereby helping keep the electrode 102 in place.

The control unit 150 supplies stimulation current to the electrodes, e.g., in the manner described in the Ghoname et al. articles. Once again, the electrical waveform provided by the control unit depends on the application. For example, in an embodiment of a system providing percutaneous neuromodulation therapy, the control unit 150 would preferably provide a current-regulated and current-balanced waveform with an amplitude of up to approximately 20 mA, frequency between approximately 4 Hz and 50 Hz, and pulse width of between approximately 50 μsec and 1 msec.

It should be noted that at no time during the electrode deployment, insertion and electrical therapy treatment processes was the sharp point of the electrode exposed to the operator or bystanders.

In an alternative embodiment, the lower wide portion of the electrode handle is formed from a rigid material and has rounded camming edges. The central annulus of patch 140 in this alternative embodiment is either compressible or has a resilient camming opening under the camming action of the electrode handle.

Figure 13:
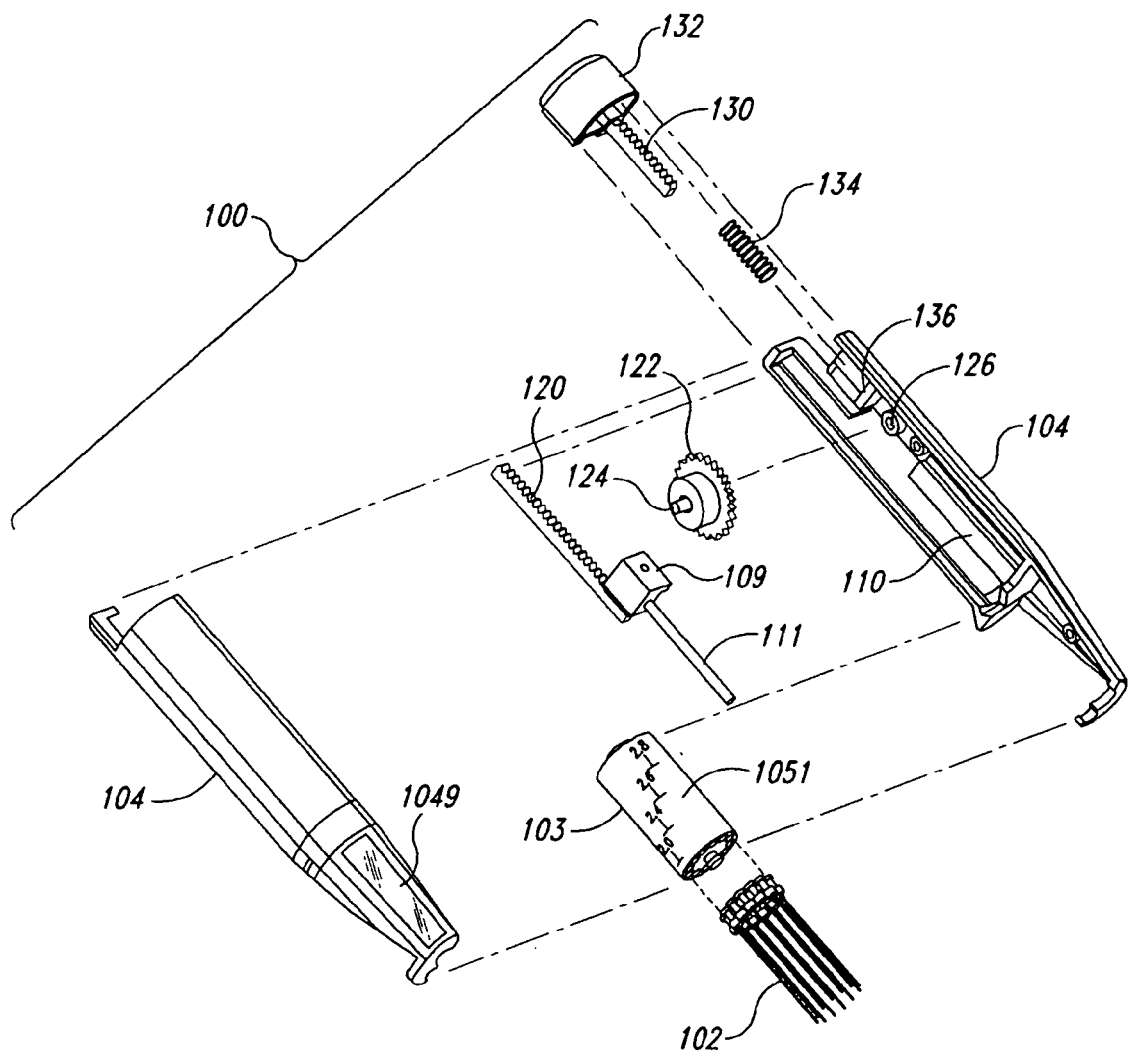
FIG. 13 is an exploded view of an electrode introducer and sharp point protection assembly of yet another embodiment of this invention.

In one embodiment, the introducer 100 can include electrodes 102 with different lengths. Accordingly, the operator can select the electrode 102 having a length corresponding to the depth beneath the patient's skin surface to which the electrode tip will deploy. In one aspect of that embodiment, each electrode 102 within the magazine 103 can have a different length. In other embodiments, the magazine 103 can include groups of electrodes 102, with electrodes 102 in each group having the same length, and with electrodes 102 from different groups having different lengths. Referring now to FIG. 13, in either embodiment, the housing 104 can include a window opening 1049 positioned to allow visual access to the magazine 103. The magazine 103 can include graduation markings 1051 which indicate the depth to which the corresponding electrode 102 will deploy. The window opening 1049 can be open or filled with a light-transmissive pane. In either embodiment, the window opening 1049 forms an at least partially light-transmissive portion of the housing 104.

In other embodiments, the introducer 100 can have other arrangements. For example, the electrodes 102 can be housed in a magazine having a linear or other non-rotational arrangement. In yet another embodiment, the magazine can house percutaneous probes other than PNT electrodes, either alone or in combination with PNT electrodes. Those other probes can include diagnostic electrical signal receptors, acupuncture needles, and/or hollow fluid delivery/withdrawal needles.

FIGS. 23-28 show a 'sharps-safe' remover according to one embodiment of this invention. A remover 200 is designed to work with the electrode and electrode patch assembly described with respect to FIGS. 13-22 above. It should be understood that the principles of the 'sharps-safe' remover 200 may apply to other electrode designs as well.

The remover 200 has a housing 202 with an aperture 204 at its distal end. A number of previously undeployed electrodes 102 are stored within the housing 202. A pair of rails 214 and 216 hold the electrodes 102 in alignment via the electrode handles 107, as shown. While this embodiment of the remover 200 is designed to provide sharps-safe removal and storage of a plurality of electrodes, the invention applies to removers designed to remove and store one or any number of electrodes.

Figure 23:
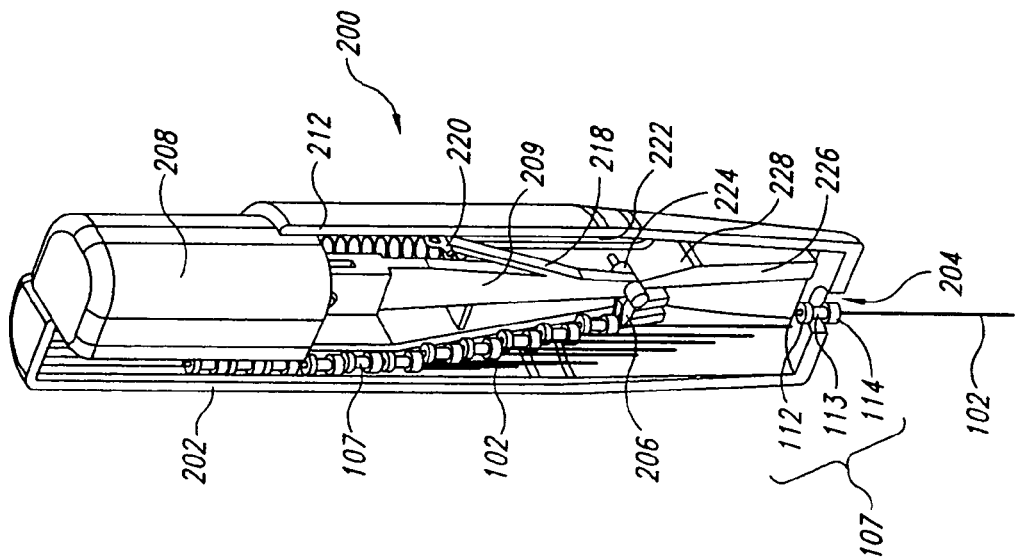
FIG. 23 is a partial sectional view of an electrode remover and sharp point protection assembly according to yet another embodiment of the invention prior to removal of an electrode.

As described above, electrodes for percutaneous electrical therapy are inserted through a patient's skin into underlying tissue with handle portions exposed above the skin. The first step in undeploying and removing an inserted electrode is to line up the exposed handle 107 of an electrode with the remover's aperture 204, as shown in FIG. 23, by placing the distal face 205 of the remover 200 against the patient's skin or against any portion of the electrode assembly (such as an adhesive patch) surrounding the electrode 102. While not shown in FIGS. 23-28, the aperture 204 is sized to surround an annular member (such as the annular member 141 discussed above) holding the electrode handle of the electrode assembly (such as that shown in FIGS. 13-22 above), the sharp point of which has been inserted through a patient's skin.

Figure 28:
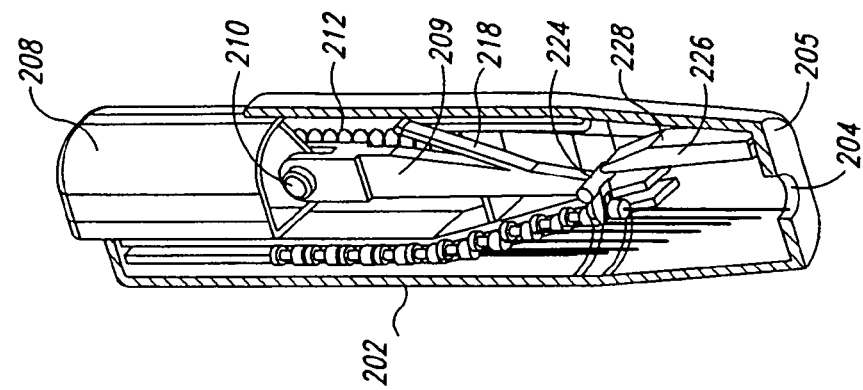
FIG. 28 is a partial sectional view of the electrode remover and sharp point protection assembly of FIG. 23 after removal of an electrode.

An electrode engagement fork 206 is pivotably attached to a longitudinally movable actuator 208 via an arm 209 and a hinged pivot 210. A coil spring 212 biases the actuator 208 upwards as shown in FIG. 28. A leaf spring 218 extends from the arm 209. A crossbar 220 at the end of the leaf spring 218 slides in a groove 222 and a corresponding groove (not shown) on the other side of the housing 202. The leaf spring 218 is in its relaxed state in the position shown in FIG. 23. In that position, a cross-bar 224 extending from the distal end of the arm 209 adjacent to the fork 206 lies at the top of a camming member 226 and a corresponding camming member (not shown) on the other side of the housing 202.

Figure 24:
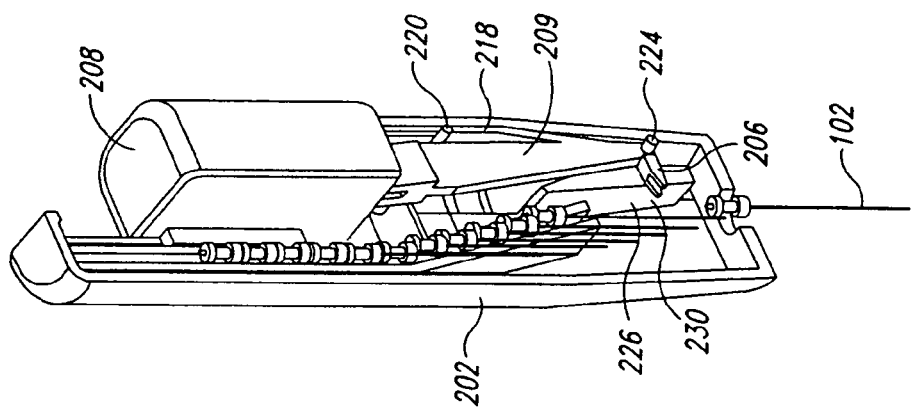
FIG. 24 is a partial sectional view of the electrode remover and sharp point protection assembly of FIG. 23 partially actuated but prior to removal of an electrode.

Downward movement of the actuator 208 (in response, e.g., to pressure from a user's thumb) against the upward force of spring the 212 moves the cross-bar 224 against a first camming surface 228 of the camming member 226, as shown in FIG. 24. The camming surface 228 pushes the cross-bar 224 of the arm 209 against the action of the leaf spring 218 as the actuator 208, the arm 209 and the fork 206 move downward.

Figure 25:
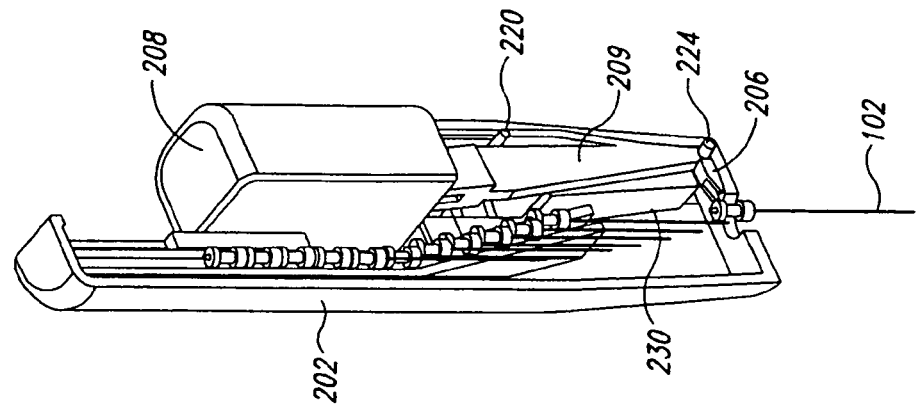
FIG. 25 is a partial sectional view of the electrode remover and sharp point protection assembly of FIG. 23 partially actuated but prior to removal of an electrode.
Figure 26:
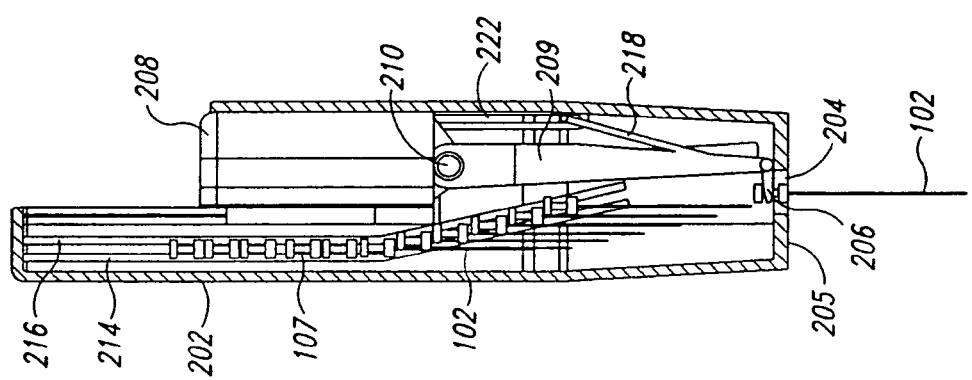
FIG. 26 is a partial sectional view of the electrode remover and sharp point protection assembly of FIG. 23 partially actuated and engaged with an electrode but prior to removal of the electrode.

FIG. 25 shows the limit of the downward movement of the fork 206. At this point, the cross-bar 224 clears the camming member 226, and the leaf spring 218 rotates the fork 206 and the arm 209 about the hinged pivot 210 to engage the fork 206 with the electrode handle 107, as shown in FIG. 26. The tine spacing of the fork 206 is shorter than the diameter of the upper wide portion 112 of the electrode handle 107 but wider than the diameter of the narrow middle portion 113 of the electrode handle 107.

Figure 27:
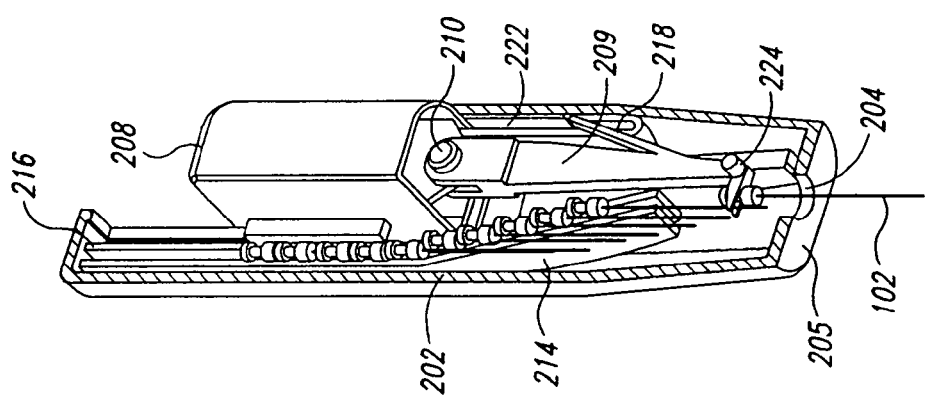
FIG. 27 is a partial sectional view of the electrode remover and sharp point protection assembly of FIG. 23 during removal of an electrode.

Releasing the actuator 208 permits the spring 212 to move the actuator 208, the arm 209 and the fork 206 proximally. The engagement between the fork 206 and the electrode handle 107 causes the electrode to begin to move proximally with the fork out of the patient and into the remover housing, as shown in FIG. 27. At this point, the cross-bar 224 is now engaged with a second camming surface 230 of the camming member 226. The camming surface 230 pushes the cross-bar 224 against the action of the leaf spring 218 in the other direction (to the left in the view shown in FIG. 27) as the electrode 102, fork and arm rise under the action of the coil spring 212.

The electrode 102 and the fork 206 continue to rise until they reach the upward limit of their permitted motion, as shown in FIG. 28. At this point, the electrode handle 107 has engaged rails 214 and 216 and the most recent electrode previously stored in the remover 200. The electrode handle 107 pushes against the previously stored electrode handle, which in turn pushes against any electrode handles stored above it in the stack. In this manner, the latest electrode removed by the remover 200 goes into the bottom of the stack of used electrodes stored in the remover 200. Now that the sharp point 108 of the electrode 102 is safely inside the housing 202, the remover 200 can be withdrawn from the site on the patient's skin through which the electrode had been inserted. Once the cross-bar 224 clears the top of the camming member 226, and the leaf spring 218 moves the arm 209 back to the center position shown in FIG. 23.

It should be noted that the remover 200 provides sharp point protection for the entire electrode undeployment and removal process. Once all electrodes have been removed, the used electrodes can be safely transported in the sharps-safe container provided by the housing 202 of the remover 200.

FIG. 29A is a partially schematic, isometric illustration of an apparatus 2900 configured to deploy a percutaneous probe 2934 to one or more depths in accordance with an embodiment of the invention. In one aspect of this embodiment, the percutaneous probe 2934 can include a therapeutic percutaneous electrode, and in other embodiments, the percutaneous probe 2934 can include a diagnostic electrode, an acupuncture needle, a drug delivery needle, a liquid extraction needle, or another sharp-ended percutaneous device. In any of those embodiments, the apparatus 2900 can include a housing 2940 in which the percutaneous probe 2934 is movably disposed. The housing 2940 can have a flange 2944 with a lower surface 2946 positioned to face toward the recipient's skin surface. The housing 2940 can further include an exit portion 2932 through which the percutaneous probe 2934 exits. In one embodiment, the exit portion 2932 can include a hollow projection 2943 that extends beyond the lower surface 2946 and receives the percutaneous probe 2934 as the percutaneous probe 2934 is deployed. The projection 2943 can stretch the recipient's skin proximate to the point at which the percutaneous probe 2934 pierces the skin and can accordingly reduce the magnitude of the sensation felt by the recipient when the percutaneous probe 2934 is deployed.

The percutaneous probe 2934 can be elastically resilient and can tend toward a neutral shape in which it is generally straight and linear. Accordingly, the percutaneous probe 2934 can have a generally straight, linear shape when deployed, and (except for a terminal portion 2929), a generally curved or arcuate shape when it is stowed within the housing 2940, as shown in FIG. 29A. When the percutaneous probe 2934 is in its stowed position, the terminal portion 2929 (including a sharp end 2933) can extend in a straight line into the projection 2943. Accordingly, the sharp end 2933 will not be biased into contact with the inner walls of the projection 2943 because the terminal portion 2929 immediately above the sharp end 2933 is generally straight and is not subjected to forces transverse to the major axis of the percutaneous probe 2934.

In a further aspect of an embodiment shown in FIG. 29A, the percutaneous probe 2934 can be supported by an actuator 2936 positioned on an actuator arm 2937. The actuator arm 2937 can be mounted to a pivot joint 2939 to rotate within the housing 2940, as shown by arrow A. The apparatus 2900 can further include an actuator tool 2960 that removably engages the actuator 2936 to move the percutaneous probe 2934 from its stowed position to one or more deployed positions. In one embodiment, for example, when the percutaneous probe 2934 includes an electrode configured to transmit and/or receive electrical signals, the actuator tool 2960 can also include a conductor 2968 which is coupleable to the control unit 10 (FIG. 1E). In another embodiment, for example, when the percutaneous probe 2934 includes a hollow needle for delivering or withdrawing liquid substances, the conductor 2968 can be replaced with a flexible fluid-tight conduit. In either embodiment, the actuator tool 2960 can be releasably engaged with the actuator 2936 to move the percutaneous probe 2934, as described in greater detail below with reference to FIGS. 29B and 29C.

Referring now to FIG. 29B, the housing 2940 can include a tool entry opening 2945 sized to receive the actuator tool 2960. The housing 2940 can further include a slot 2941 sized to allow the actuator tool 2960 to move along the arcuate path indicated by arrow A for deploying and retracting the percutaneous probe 2934. As described in greater detail below with reference to FIG. 29C, the slot 2941 can be sized to prevent the actuator tool 2960 from being removed unless the actuator tool 2960 is positioned at the tool entry opening 2945. Accordingly, the apparatus 2900 can prevent the actuator tool 2960 from being removed from the housing 2940 while the percutaneous probe 2934 is deployed.

The percutaneous probe 2934 can be selectively deployed to any of a number of positions, depending upon how far the actuator tool 2960 is moved away from the tool entry opening 2945. In one aspect of the embodiment, the housing 2940 can include graduation markings 2951 to aid the operator in determining how deep the percutaneous probe 2934 is deployed at any time. In a further aspect of the embodiment, the slot 2941 can include detents 2933 positioned at selected intervals to releasably lock the actuator tool 2960 at predetermined positions. Accordingly, the actuator tool 2960 can include an engaging portion, such as a tab (not visible in FIG. 29B) that is releasably received by the detents 2933. The actuator tool 2960 can be slightly biased (for example, with a spring) towards the detents 2933 so that it "clicks" into place as it passes each detent 2933. The operator exerts a slight transverse pressure on the actuator tool 2960 away from the detents 2933 to disengage the actuator tool 2960 from the detents 2933 for further deploying and/or stowing the percutaneous probe 2934.

In other embodiments, the apparatus 2900 can include other releasable locking arrangements. For example, in one embodiment, the housing 2940 can include a plurality of apertures 2952 at selected positions, with each aperture 2952 sized to removably receive a pin 2950. The operator can position the pin 2950 in the aperture that corresponds to the desired deployment depth, and the pin 2950 can arrest motion of the actuator 2936 beyond the selected position.

Referring now to FIG. 29C, the actuator 2936 can include a receiving portion 2931 positioned to removably receive the actuator tool 2960. In one aspect of the embodiment, the receiving portion 2931 can include a contact opening 2935. The actuator tool 2960 can include a conductive pin 2966 that fits into the contact opening 2935 and provides electrical and physical contact with that portion of the percutaneous probe 2934 in the contact opening 2935. In one aspect of the embodiment, the contact pin 2966 can be sized and positioned to exert a transverse force (indicated by arrow T) on the percutaneous probe 2934 to form a snug fit with the percutaneous probe 2934.

Referring now to FIGS. 29B and 29C together, the actuator tool 2960 can further include a retainer 2961 that is small enough to be received in the tool entry opening 2945 of the housing 2940, but too large to be pulled out through the slot 2941. Accordingly, in one embodiment, the actuator tool 2960 (a) can be inserted into the tool entry opening 2945 to make electrical and physical contact with the percutaneous probe 2934, (b) can drive the actuator 2936 as indicated by arrow A, but (c) cannot be withdrawn from the housing 2940 until the actuator tool 2960 is returned to the tool entry opening 2945.

One feature of an embodiment of the apparatus described above with reference to FIGS. 29A-29C is that the operator can easily select one or more deployment depths for a percutaneous probe without requiring more than a single apparatus. Accordingly, a single percutaneous probe 2934 can have available multiple percutaneous lengths (e.g., the length of the percutaneous probe positioned within the recipient). An advantage of this feature is that it can be easier and less time consuming for the operator to choose a deployment depth because the operator's choice does not also require a choice as to which apparatus to use. Another advantage is that the operator can change the deployment depth even after the apparatus is attached to the recipient and the percutaneous probe is deployed. This can in turn make the treatment session shorter and more pleasant for the recipient.

Figure 30B:
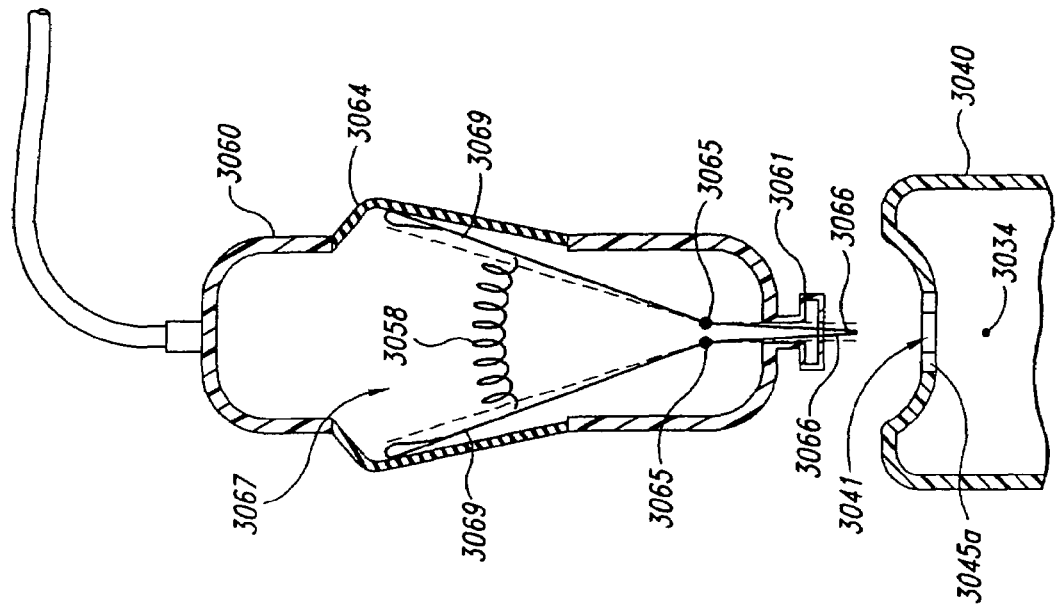
FIGS. 30A-30B illustrate a percutaneous apparatus configured in accordance with another embodiment of the invention.
Figure 30A:
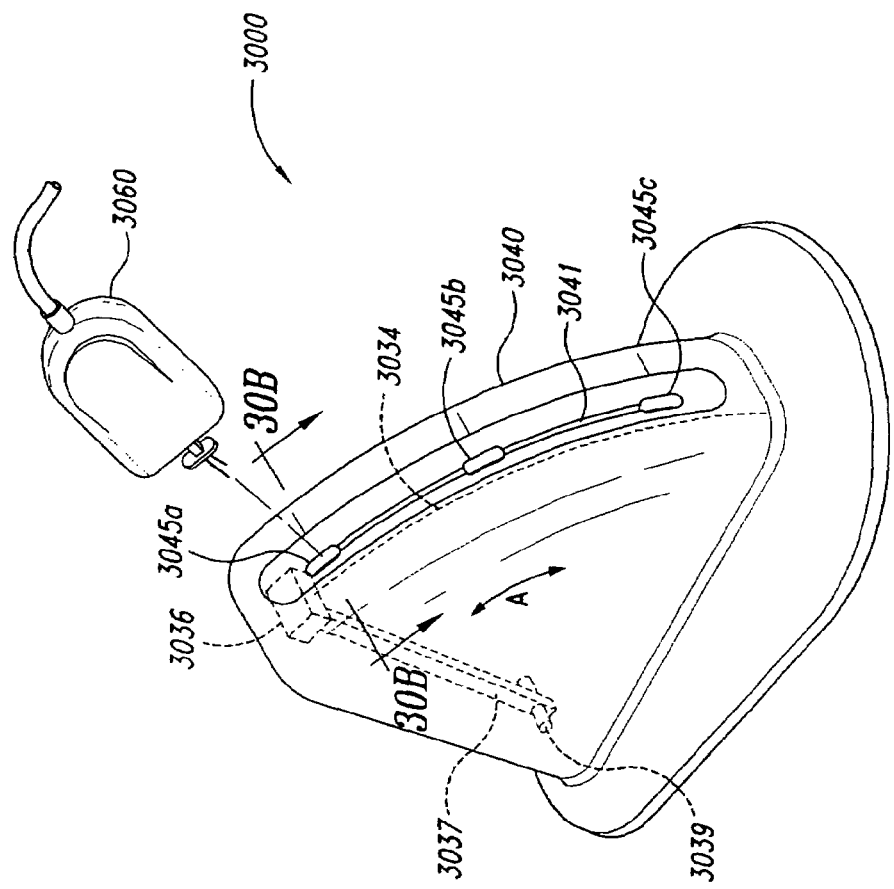

FIG. 30A is a partially schematic, isometric illustration of an apparatus 3000 configured to deploy a percutaneous probe 3034 to at least one of a plurality of depths. In one aspect of the embodiment, the percutaneous probe 3034 is housed in a housing 3040 and carried by an actuator 3036, which is in turn attached to an actuator arm 3037. The actuator arm 3037 pivots relative to the housing 3040 about a pivot point 3039 to deploy the percutaneous probe 3034 out of the housing 3040 in a manner generally similar to that described above with reference to FIGS. 29A-29C. In a further aspect of this embodiment, the housing 3040 can include a plurality of tool entry openings 3045 (three are shown in FIG. 30A as tool entry openings 3045a-3045c) spaced apart along a slot 3041 at selected intervals corresponding to selected deployment depths for the percutaneous probe 3034. The actuator tool 3060 can be inserted into any of the tool entry openings 3045 to engage the percutaneous probe 3034 at a selected position along its length. The actuator tool 3060 can then be moved along the slot 3041 to deploy the percutaneous probe 3034 to a corresponding selected depth in the recipient's tissue.

FIG. 30B is a partially schematic, cross-sectional illustration of a portion of the housing 3040 and the actuator tool 3060 in accordance with the embodiment of the invention, taken substantially along line 30B-30B of FIG. 30A. In one aspect of the embodiment, the actuator tool 3060 can include a clamp 3067 having two clamp arms 3069, each pivotable about a clamp pivot 3065. Each clamp arm 3069 can further include a contact portion 3066 which extends through a retainer 3061. A spring 3058 can force the clamp arms 3069 apart from each other. A flexible cover 3064 can be disposed over the clamp arms 3069 to protect the clamp arms 3069 while allowing them to move.

To connect the actuator tool 3060 with the percutaneous probe 3034, the operator can squeeze the clamp arms 3069 together, allowing the contact portions 3066 to spread apart (as indicated in dashed lines in FIG. 30B) by a distance that still allows the contact portions 3066 to fit through the tool entry opening 3045a. The operator then lowers the retainer 3061 and the contact portions 3066 into the tool entry opening 3045a to position the contact portions 3066 around the percutaneous probe 3034. The operator then releases the clamp arms 3069, allowing the contact portions 3066 to move toward each other and clamp the percutaneous probe 3034. The operator can then move the actuator tool 3060 relative to the housing 3040 (as indicated in FIG. 30A by arrow A) to deploy and stow the percutaneous probe 3034.

FIG. 31 A is a rear isometric view of a percutaneous apparatus 3100 having a housing 3140 supporting a percutaneous probe 3134. The housing 3140 can further include a slot 3141. The operator can slide an actuator tool 3160 transversely into the slot 3141 to engage the percutaneous probe 3134, and can then slide the actuator tool 3160 axially within the slot 3141 to deploy and stow the percutaneous probe 3134. The housing 3140 can include housing finger detents 3147, and the actuator tool 3160 can include tool finger detents 3159 which allow the operator to positively engage the housing 3140 and the actuator tool 3160, respectively, while moving the percutaneous probe 3134.

Figure 31A:
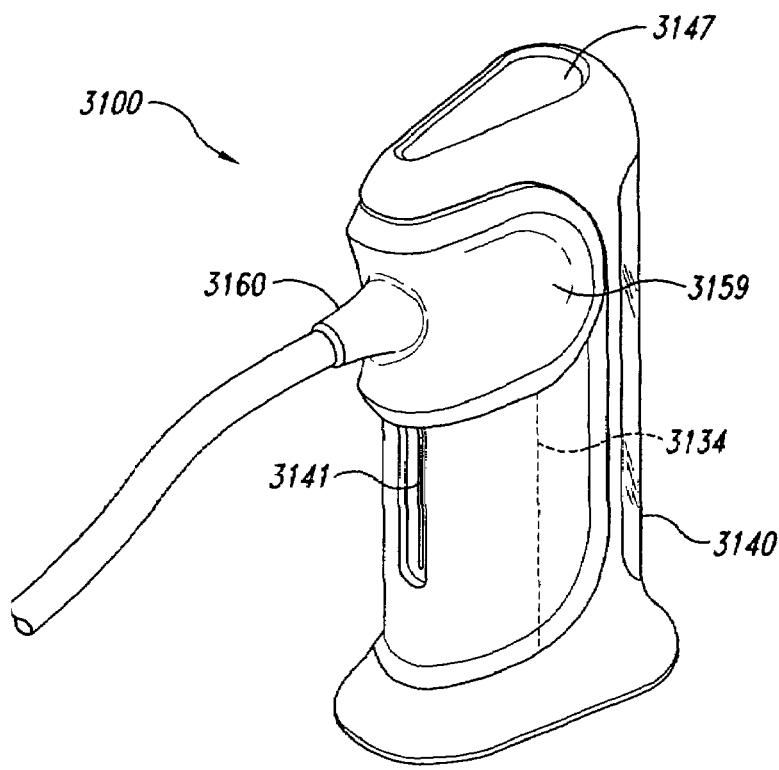
FIGS. 31A-31B illustrate a percutaneous apparatus having a linear slider configured in accordance with an embodiment of the invention.
Figure 31B:
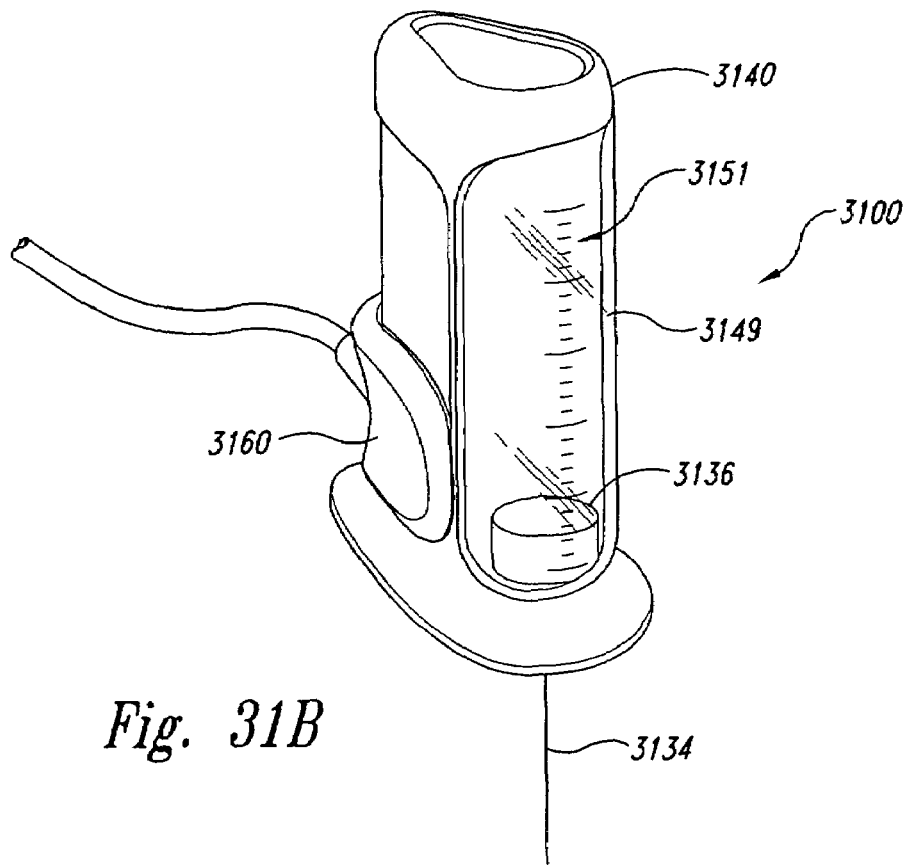

FIG. 31B is a front isometric view of an embodiment of the percutaneous apparatus 3100 shown in FIG. 31A. In one aspect of the embodiment, the housing 3140 can include an at least partially light transmissive window 3149 through which the percutaneous probe 3134 and a supporting actuator 3136 are visible. The actuator tool 3160 can releasably engage the actuator 3136 and/or the percutaneous probe 3134 via an engagement arrangement (not visible in FIG. 31B) generally similar to any of those described above. The housing 3140 can further include graduation markings 3151 to indicate the depth to which the percutaneous probe 3134 is deployed. In one aspect of the embodiment, the window 3149 can include an at least partially light transmissive pane, for example, a clear plastic pane. In another embodiment, window 3149 can be open to allow visual access to the percutaneous probe 3134 within the housing. An advantage of both embodiments is that the window 3149 can make it easier for the practitioner to deploy the percutaneous probe 3134 to a pre-selected target position.

Figure 32:
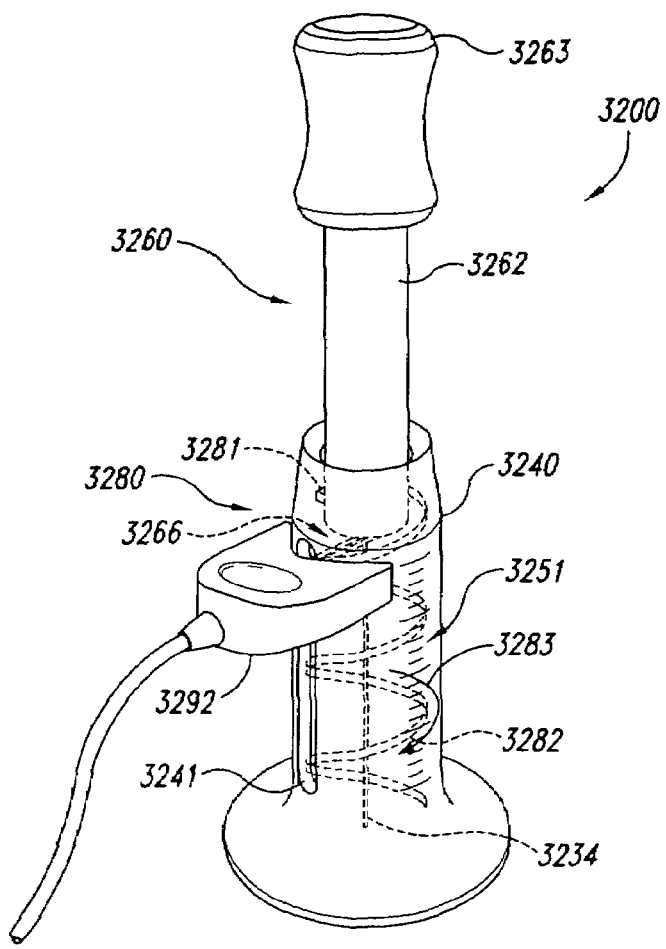
FIG. 32 illustrates a percutaneous apparatus having depth control determined by a twisting motion.

FIG. 32 is a partially schematic, side isometric view of a percutaneous apparatus 3200 having an actuator tool 3260 movably coupled to a housing 3240, and an electrical connector 3292 that is both movably and removably coupled to the housing 3240. In one aspect of the embodiment, the actuator tool 3260 includes a handle 3263 and a plunger 3262 that is fixedly connected to a percutaneous probe 3234. In a further aspect of the embodiment, the housing 3240 can include graduation markings 3251 to provide a visual indication of the depth to which the percutaneous probe 3234 is deployed in a recipient's tissue.

The apparatus 3200 can also include a depth control device 3280. In one embodiment, the depth control device 3280 can include a tab 3281 depending from the plunger 3262 and engaged with a helical slot 3282 in a wall of the housing 3240. As the plunger 3262 is depressed and rotated, the tab 3281 tracks in the helical slot 3282, following a helical path 3283 which controls the depth to which the percutaneous probe 3234 is deployed. In a further aspect of the embodiment, friction between the tab 3281 and the helical slot 3282 can prevent the plunger 3262 from descending further than desired along the helical path 3283 unless the operator applies a deliberate force to the handle 3263. In other embodiments, the depth control device 3280 can include detents or other locking mechanisms to prevent unintended motion of the plunger 3262 once the percutaneous probe 3234 has reached a target deployment depth.

In another aspect of the foregoing embodiment, the electrical connector 3292 can have a contact portion 3266 positioned to releasably contact the percutaneous probe 3234. In one aspect of the embodiment, the contact portion 3266 can have an arrangement generally similar to that described above with reference to FIG. 30B, and in other embodiments, the contact portion 3266 can have other arrangements. In any of those embodiments, the contact portion 3266 can maintain electrical contact with the percutaneous probe 3234 as the percutaneous probe 3234 descends and rotates during deployment. For example, the electrical connector 3292 can move linearly in a connector slot 3241 as the plunger 3262 follows the helical path 3283. As the percutaneous probe 3234 rotates relative to the contact portion 3266, it remains in electrical contact with the contact portion 3266.

Figure 33:
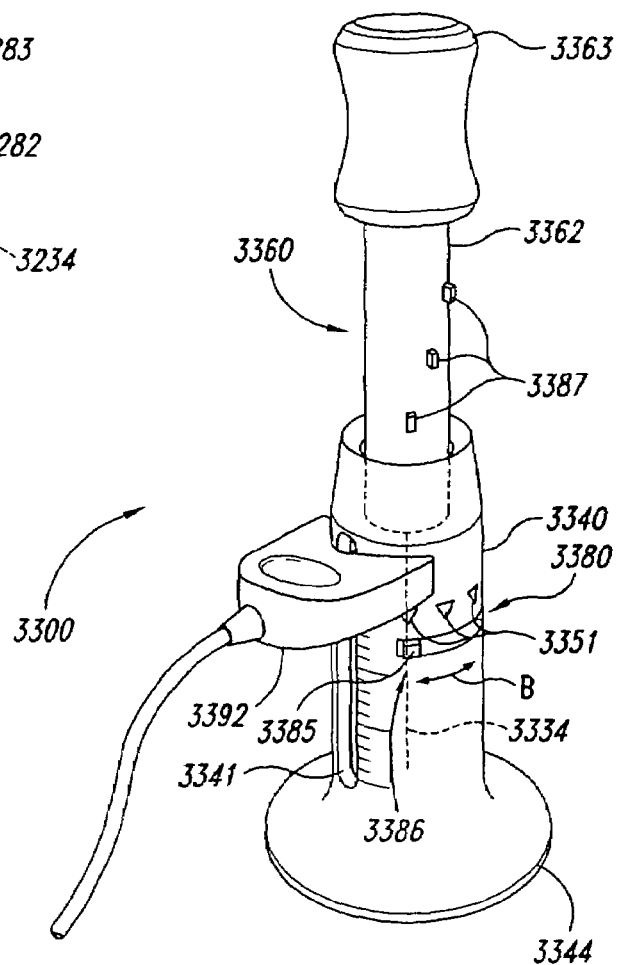
FIG. 33 illustrates a percutaneous apparatus having a pre-adjustable depth control portion in accordance with an embodiment of the invention.

FIG. 33 is a partially schematic, isometric illustration of a percutaneous apparatus 3300 having an actuator tool 3360 and an electrical connector 3392 arranged in accordance with another embodiment of the invention. In one aspect of the embodiment, the actuator 3360 includes a plunger 3362 positioned to move a percutaneous probe 3334 linearly within a housing 3340. In a further aspect of the embodiment, the percutaneous apparatus 3300 can include a depth control device 3380 which can be pre-set to a selected depth before deploying the percutaneous probe 3334. For example, the depth control device 3380 can include a pre-adjustable portion 3386 having an adjustable first stop member 3385. The first stop member 3385 can be moved circumferentially, as indicated by arrow B, to align with one of a plurality of indicator markings 3351 corresponding to a selected deployment depth. The depth control device 3380 can further include second stop members 3387 depending from the plunger 3362. The second stop members 3387 are spaced apart from each other axially and circumferentially so that each one will only engage the first stop member 3385 when the first stop member 3385 is in one of the selected positions. Accordingly, the operator can (a) move the first stop member 3385 to a location corresponding to the desired deployment depth, and then (b) move the plunger 3362 downwardly until the corresponding second stop member 3387 engages the first stop member 3385. An advantage of that arrangement is that the practitioner can use a single smooth motion to deploy the percutaneous probe 3334, regardless of its target depth.

Figure 34:
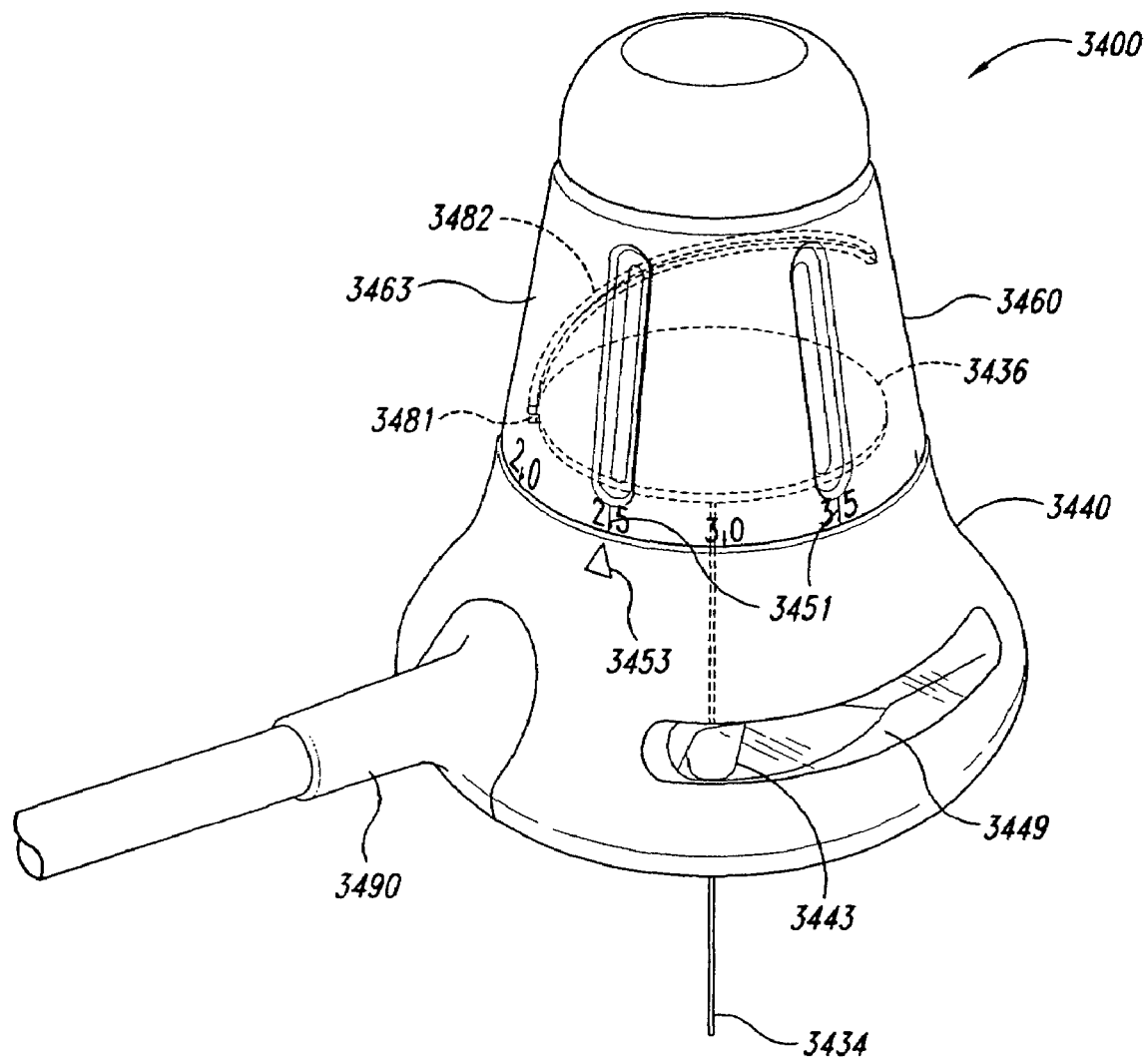
FIG. 34 illustrates a percutaneous apparatus having a viewing slot in accordance with an embodiment of the invention.

FIG. 34 is a partially schematic, top isometric view of a percutaneous apparatus 3400 having a housing 3440, a percutaneous probe 3434 disposed within the housing 3440, and an actuator 3436 carrying the percutaneous probe 3434. The apparatus 3400 can further include an actuator tool 3460 that rotates relative to the housing 3440. In one aspect of the embodiment, the actuator tool 3460 can have a helical slot 3482 which receives a tab 3481 depending from the actuator 3436. Accordingly, an operator can rotate the actuator tool 3460 to deploy and retract the percutaneous probe 3434.

In a further aspect of the embodiment, the housing 3440 can include a depth indicator marking 3453 and the actuator tool 3460 can include graduation markings 3451 which allow the operator to visually determine the depth to which the percutaneous probe 3434 is being deployed. The housing 3440 can further include an at least partially light transmissive viewing window 3449 which allows the operator visual access to a projection 3443 through which the percutaneous probe 3434 passes as it enters the recipient's tissue. In one aspect of the embodiment, the viewing window 3449 can be an open slot and in other embodiments, the viewing window 3449 can include an at least partially light transmissive pane. An electrical connector 3490 can provide electrical contact with the percutaneous probe 3434 (for example, in a manner generally similar to that described above with reference to FIG. 32) as the probe 3434 descends and rotates during deployment.

Figure 35A:
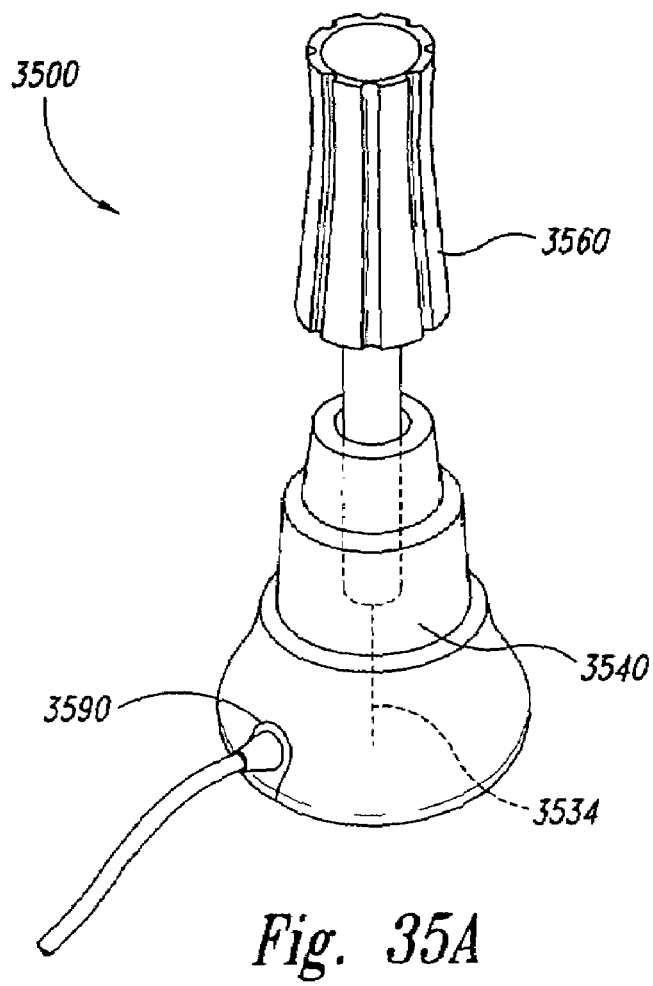
Figure 35B:
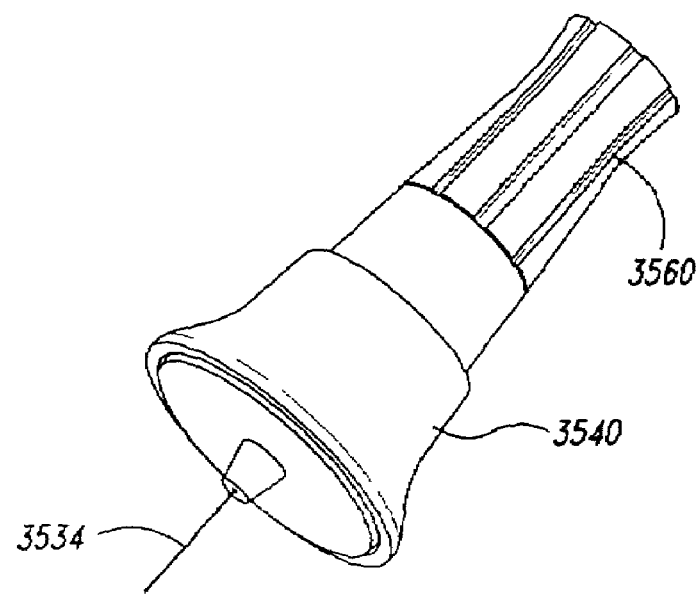

FIG. 35A is a partially schematic, top isometric illustration of a percutaneous apparatus 3500 having an actuator tool 3560 and an electrical connector 3590 configured in accordance with another embodiment of the invention. In one aspect of the embodiment, the actuator tool 3560 is movably but unreleasably attached to the housing 3540 to deploy and retract a percutaneous probe 3534. The electrical connector 3590 can have a ringshape configuration and can be attached to the housing 3540 by sliding the electrical connector 3590 over the housing 3540 from top to bottom. The actuator tool 3560 can be moved axially from a stowed position shown in FIG. 35A to a deployed position shown in FIG. 35B. In one embodiment, the actuator tool 3560 rotates to move along a helical actuation path, and in another embodiment, the actuator tool 3560 moves along a straight linear path. In either embodiment, the apparatus 3500 can include graduation markings and/or a depth control device generally similar to those described above to help the operator monitor and/or control the depth to which the percutaneous probe 3534 is deployed.

Figure 36A:
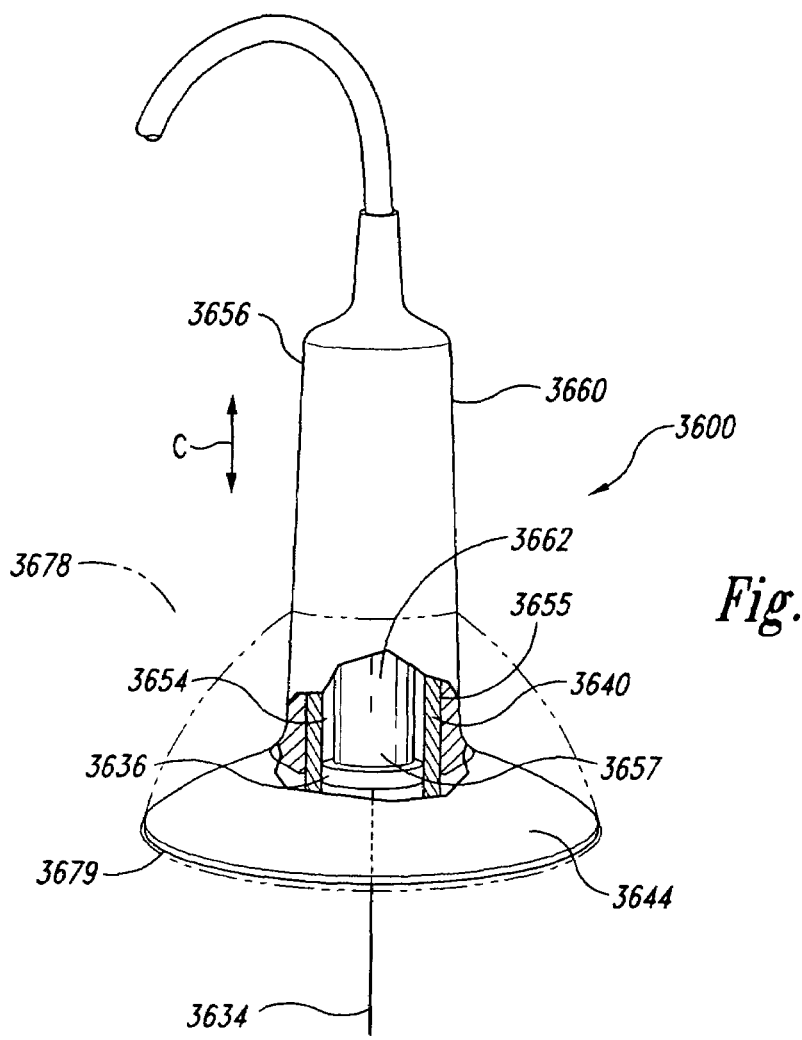

FIGS. 36A-38B illustrate percutaneous apparatuses having housings and actuator tools that at least partially surround the housings when operated in accordance with further embodiments of the invention. Referring first to FIG. 36A, an apparatus 3600 can include a housing 3640 having an outwardly extending flange 3644 and an adhesive attachment portion 3679 for releasably attaching the housing 3640 to a recipient's skin. The apparatus 3600 can further include a percutaneous probe 3634 carried by an actuator 3636. An actuator tool 3660 can be releasably coupled to the actuator 3636 via a plunger 3662 having an engaging portion 3657. The engaging portion 3657 can be offset inwardly from a grip portion 3656 of the actuator tool 3660, with an annular housing slot 3654 positioned around the engaging portion 3657. As the operator grasps the grip portion 3656 and moves the actuator tool 3660 downwardly to deploy the percutaneous probe 3634, at least part of the actuator tool 3660 (e.g., the grip portion 3656) can at least partially cover an exterior surface 3655 of the housing 3640. An advantage of this arrangement is that the grip portion 3656 is laterally displaced from the housing 3640 when the actuator tool 3660 is in the deployed position, reducing the overall height of the apparatus 3600. Accordingly, the operator may be less likely to inadvertently contact or jostle the apparatus 3600 while the percutaneous probe 3634 is deployed.

In a further aspect of the embodiment, the actuator tool 3660 can include an attachment cover portion 3678 (shown in phantom lines in FIG. 36A) which extends outwardly over the flange 3644 and the attachment portion 3679 when the actuator tool 3660 is in the deployed position. One feature of the arrangement is that the attachment portion 3679 is inaccessible beneath the attachment portion cover 3678 when the actuator tool 3660 is in the deployed position. An advantage of that feature is that the attachment portion cover 3678 can reduce the likelihood for an operator to detach the housing 3640 from the recipient while the percutaneous probe 3634 is deployed in the recipient.

Figure 36B:
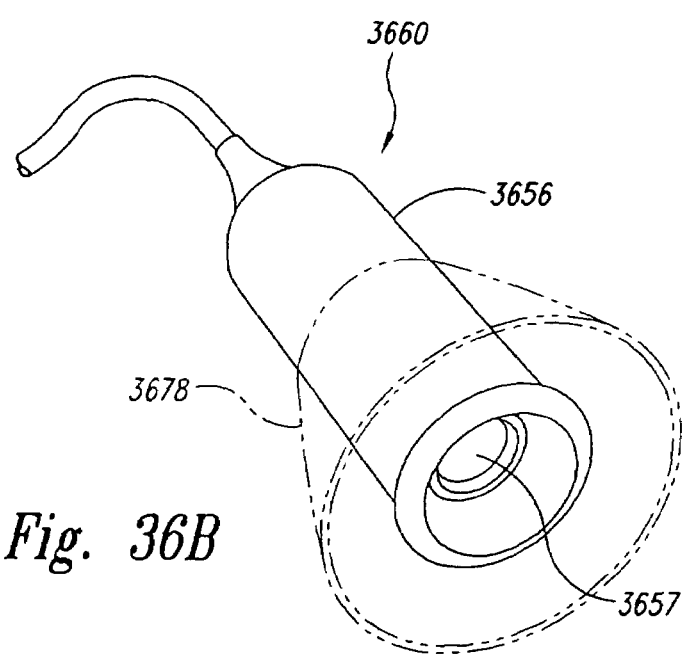

FIG. 36B is a partially schematic, isometric illustration of the actuator tool 3660 when separated from the housing 3640 (FIG. 36A). For purposes of illustration, details of the electrical and mechanical connection between the engaging portion 3657 and the actuator 3636 (FIG. 36A) are not shown in FIG. 36B. As shown in FIG. 36B, the grip portion 3656 can extend outwardly around the engaging portion 3657. An advantage of that feature is that the grip portion 3656 can protect the engaging portion 3657 from incidental contact prior to connecting the actuator tool 3660 to the actuator 3636. When the actuator tool 3660 further includes the attachment portion cover 3678, the attachment portion cover 3678 can further protect the engaging portion 3657 from incidental contact.

FIGS. 37A-37B are schematic illustrations of an apparatus 3700 having a housing 3740 and an actuator tool 3760 that covers at least a portion of the housing 3740 when the actuator tool 3760 has deployed a percutaneous probe 3734. In one aspect of the embodiment, the actuator tool 3760 includes an engaging portion 3657 and a grip portion 3756 disposed outwardly from the engaging portion 3657. In one aspect of the embodiment, the grip portion 3756 does not surround the entire length of the engaging portion 3657. However, because the grip portion 3756 is offset primarily outwardly (rather than upwardly) from the housing 3740 when it is deployed, it does not add significantly to the overall height of the apparatus when in the deployed position, in a manner generally similar to that described above with reference to FIGS. 36A-36B.

FIGS. 38A-38B illustrate an apparatus 3800 that includes a removable actuator tool 3860 configured in accordance with another embodiment of the invention. The apparatus 3800 can include a housing 3840 carrying a percutaneous probe 3834. The actuator tool 3860 can have a grip portion 3856, and a housing slot 3854 that receives at least an upper portion of the housing 3840 when the actuator tool 3860 deploys the percutaneous probe 3834. Accordingly, the grip portion 3856 can be laterally (rather than vertically) offset from the housing 3640 when the percutaneous probe 3834 is deployed. As described above, that arrangement can reduce the extent to which the actuator tool 3860 adds to the overall height of the apparatus 3800 when the percutaneous probe is deployed.

Figure 39A:
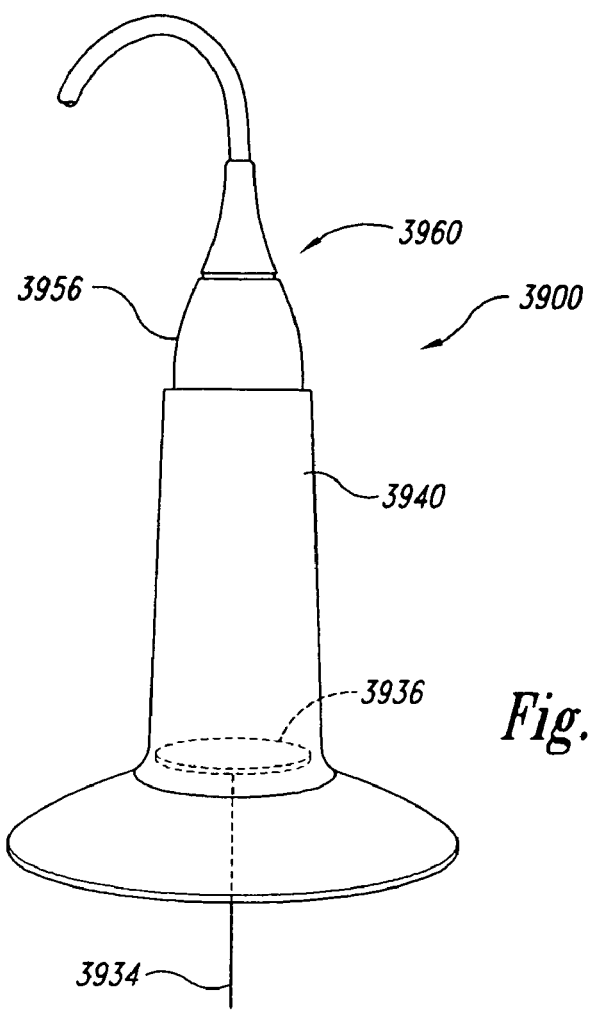
Figure 39B:
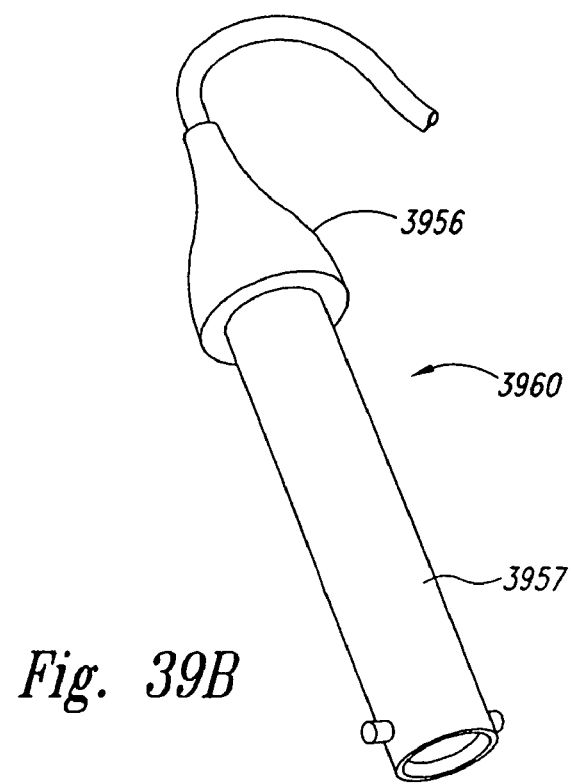

FIGS. 39A-39B illustrate an apparatus 3900 having a percutaneous probe 3934 supported by an actuator 3936 within a housing 3940. An actuator tool 3960 having a generally slender profile can include an engaging portion 3957 configured to engage the actuator 3936 to deploy the percutaneous probe 3934 into the recipient. In one aspect of the embodiment, the actuator tool 3960 includes a grip portion 3956 that is tapered in an upward direction to reduce the volume of the grip portion 3956 and therefore, the likelihood that it will interfere with adjacent apparatuses placed on the recipient's skin.

FIGS. 40A-40D are partially schematic illustrations of an apparatus 4000 having a locking device 4080 in accordance with an embodiment to the invention. Beginning with FIG. 40A, the apparatus 4000 can include a housing 4040 formed from two housing halves 4040a and 4040b. The housing 4040 can movably carry an actuator 4036 formed from two actuator halves 4036a and 4036b. The actuator 4036 can carry a percutaneous probe 4034 for movement relative to the housing 4040 between a stowed position and a deployed position. In one aspect of the embodiment, the actuator 4036 can include a guide slot 4082a which engages a corresponding actuator guide 4083 positioned in the housing 4040. Accordingly, the actuator guide 4083 can be received in the guide slot 4082a to control the motion of the actuator 4036 in an axial direction.

In another aspect of the embodiment, the actuator guide 4083 can include one or more notches configured to releasably lock the actuator 4036. For example, the actuator guide 4083 can include an undeployed notch 4084a which locks the actuator 4036 in its undeployed or stowed position. The actuator guide 4083 can optionally include a plurality of deployed notches 4084b which can lock the actuator 4036 in a corresponding plurality of deployed positions. In any of those embodiments, the actuator 4036 can include a locking device 4080, such as a locking disk 4081. The locking disk 4081 can include a guide slot 4082b which also receives and slides along the actuator guide 4083 as will be described in greater detail below with reference to FIGS. 40C and 40D. The locking disk 4081 can be selectively received in the notches 4084 to prevent axial movement of the actuator 4036.

The apparatus 4000 can further include an actuator tool 4060 having an engaging portion 4062 that is releasably received in the housing 4040 to move the actuator 4036 relative to the housing 4040. In one aspect of the embodiment, the engaging portion 4062 can include a probe aperture 4067 which provides electrical contact between the percutaneous probe 4034 and the controller 10 (FIG. 1E). The engaging portion 4062 can also include tabs 4065 that releasably secure the actuator tool 4060 to the actuator 4036.

Figure 40A:
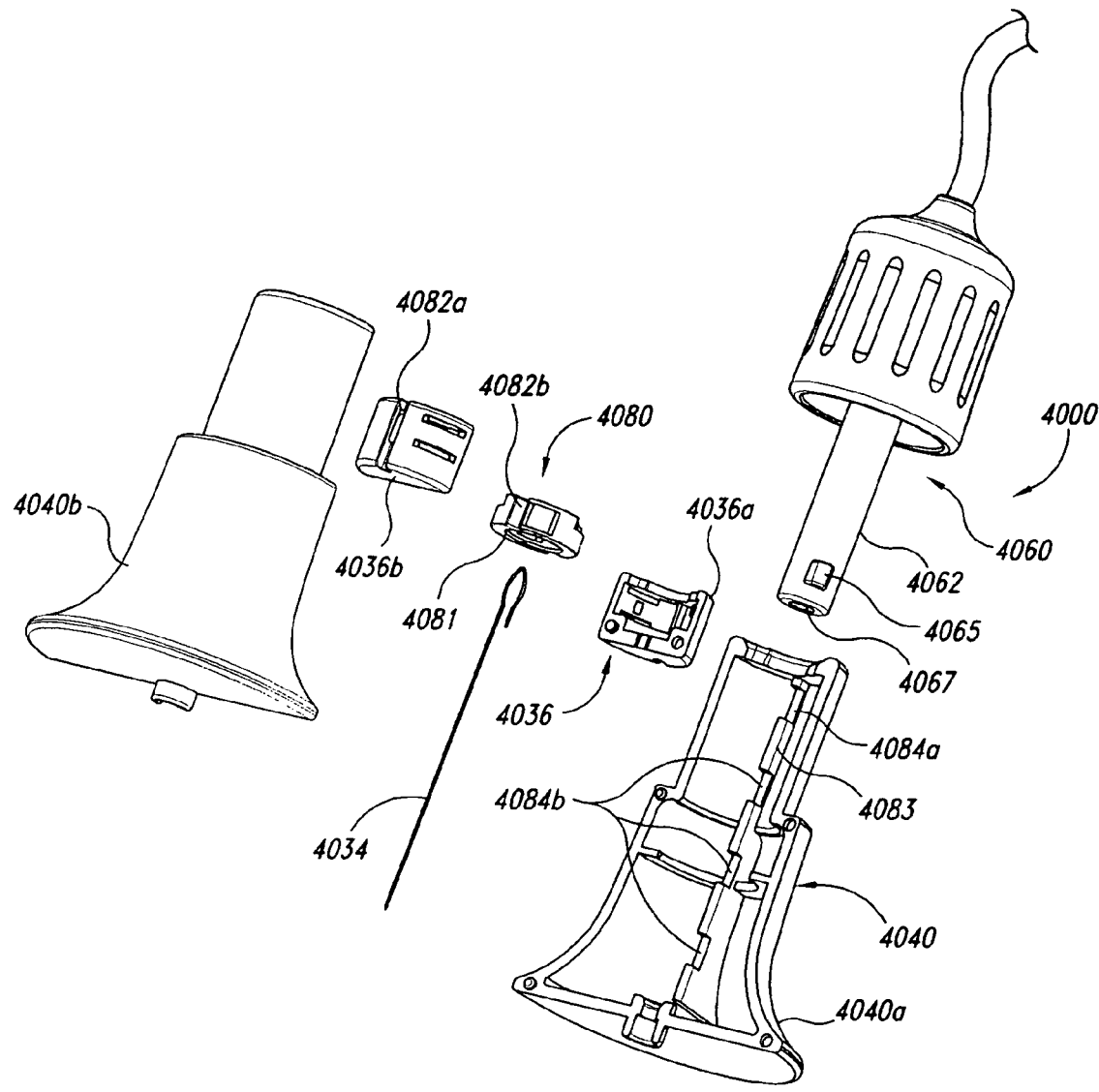
FIGS. 40A-41D illustrate percutaneous apparatuses having locking devices in accordance with yet further embodiments of the invention.
Figure 40B:
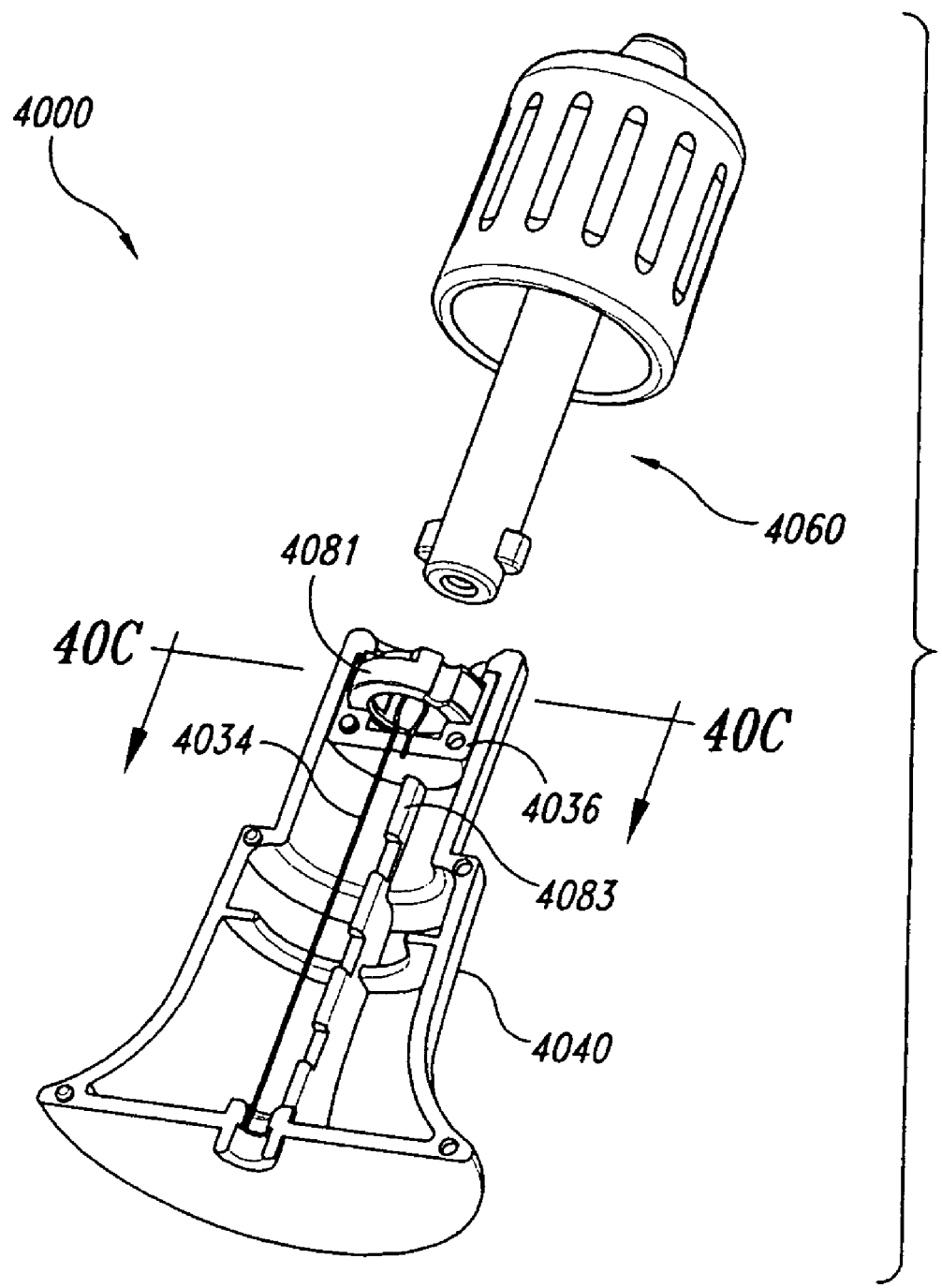

FIG. 40B illustrates a partially cutaway view of the apparatus 4000 with the actuator 4036 and the locking disk 4081 received in the housing 4040. The actuator tool 4060 is positioned in axial alignment with the housing 4040 to releasably engage the actuator 4036. In that position, the locking disk 4081 is engaged with the undeployed notch 4084a (hidden from view in FIG. 40B) to prevent motion of the actuator 4036 until the actuator tool 4060 has properly engaged the actuator 4036.

Figure 40C:
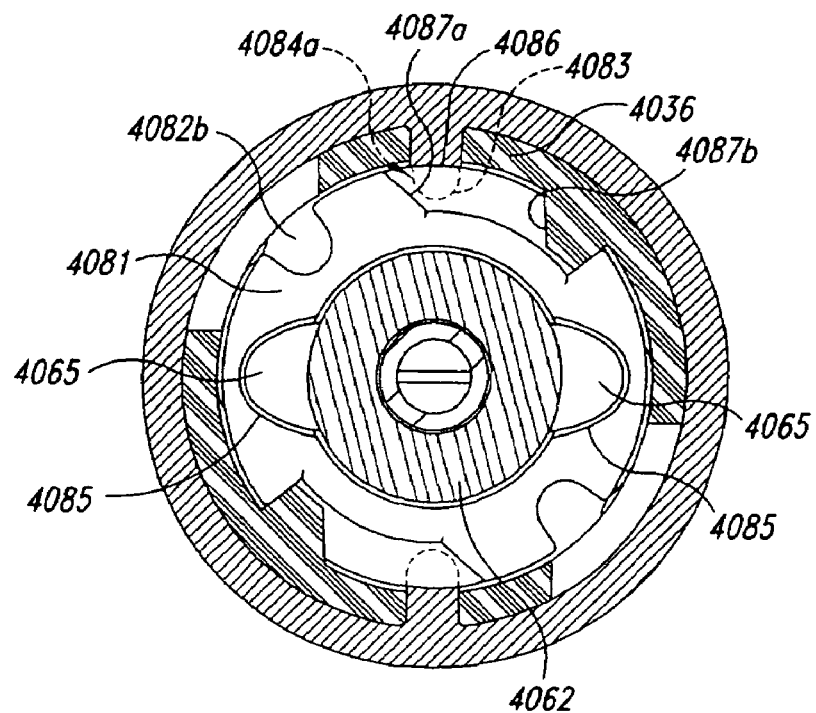

FIG. 40C is a partially schematic, cross-sectional view of the apparatus 4000, taken substantially along lines 40C-40C of FIG. 40B, with the engaging portion 4062 of the actuator tool 4060 releasably engaged with the actuator 4036. As shown in FIG. 40C, the tabs 4065 of the engaging portion 4062 are received in corresponding tab apertures 4085 of the locking disk 4081. The guide slot 4082b of the locking disk 4081 is rotationally offset from the actuator guide 4083. Accordingly, a locking portion 4086 of the locking disk 4081 is received in the notch 4084a of the actuator guide 4083 to prevent axial motion of the actuator 4036. The locking disk 4081 can also include a stop surface 4087a, which is spaced apart from a corresponding stop surface 4087b of the actuator 4036 as shown in FIG. 40C. When the locking disk 4081 is rotated, the stop surfaces 4087a and 4087b can engage each other to prevent further rotation of the locking disk 4081, as described in greater detail below with reference to FIG. 40D.

Figure 40D:
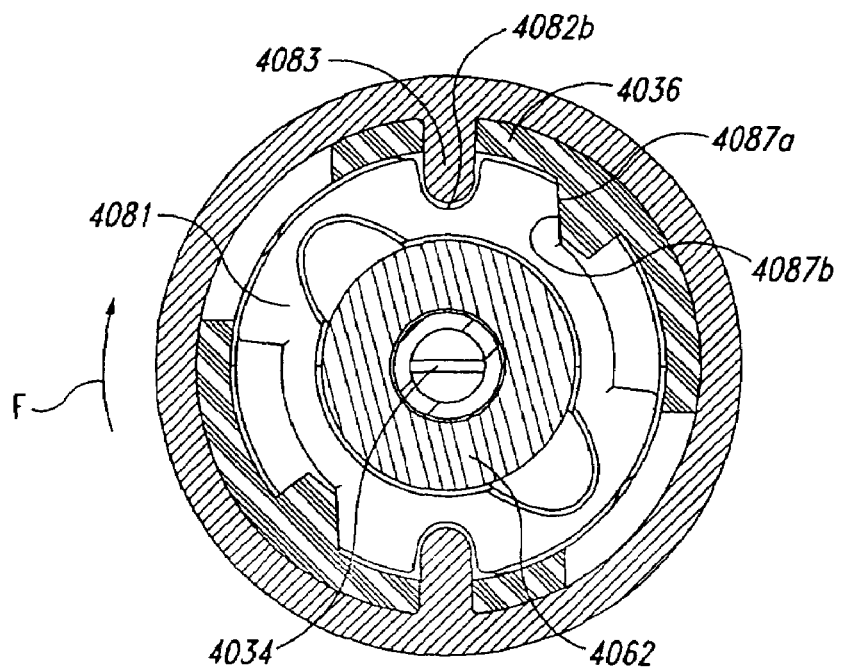

Referring now to FIG. 40D, the engaging portion 4062 and the locking disk 4081 have been rotated as a unit, as indicated by arrow F until the stop surface 4087a of the locking disk 4081 engages the corresponding stop surface 4087b of the actuator 4036. In that orientation, the guide slot 4082b of the locking disk 4081 is aligned with the actuator guide 4083. Accordingly, the engaging portion 4062, the locking disk 4081 and the actuator 4036 can be moved axially (i.e., normal to the plane of FIG. 40D) to deploy and/or stow the percutaneous probe 4034.

Figures 41A, 41B:
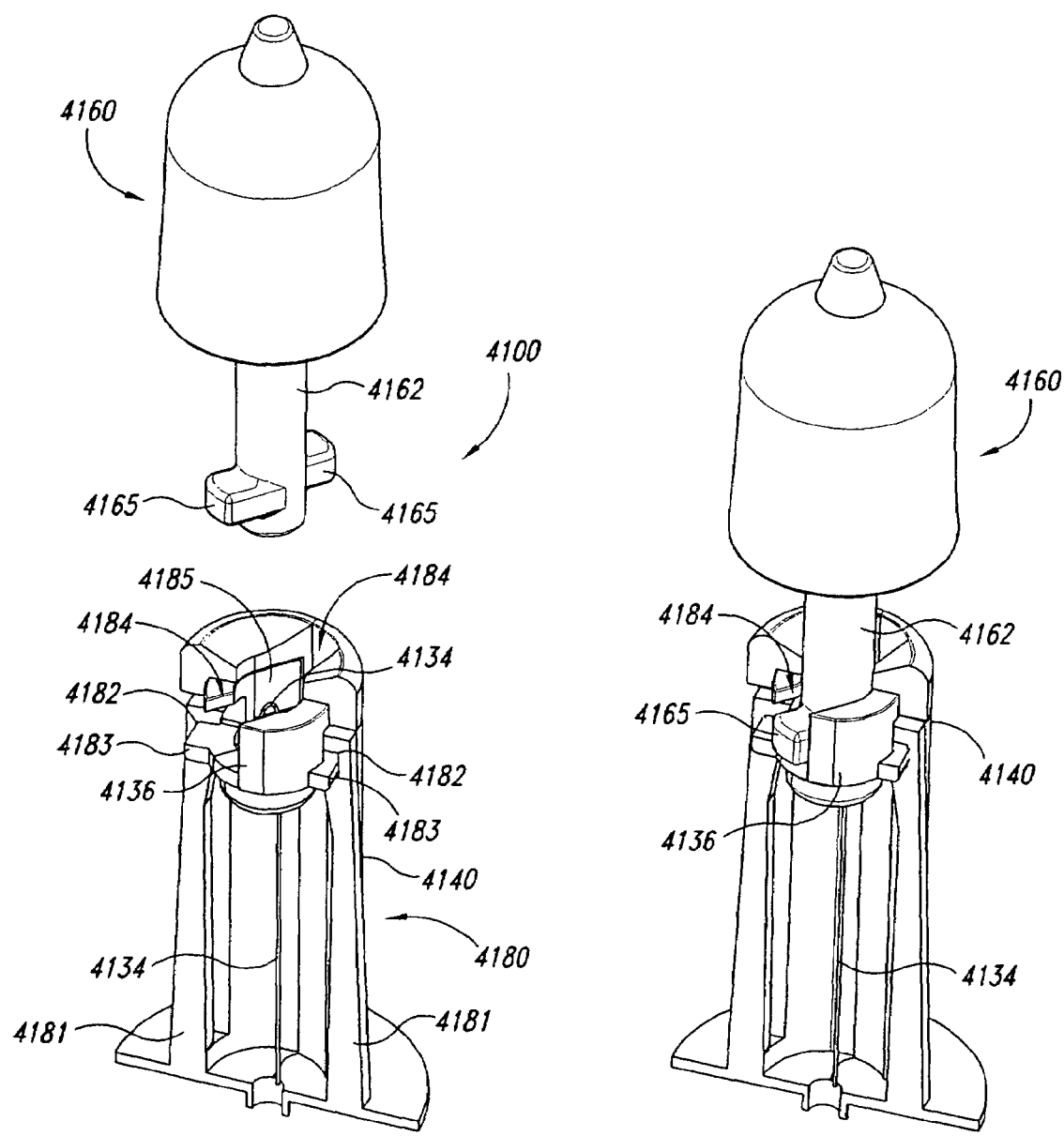

FIGS. 41A-41D are partially schematic illustrations of an apparatus 4100 having a locking device 4180 configured in accordance with another embodiment of the invention. Beginning with FIG. 41A, the apparatus 4100 can include a housing 4140. An actuator 4136 carrying a percutaneous probe 4134 is positioned in the housing 4140 for movement between a stowed position and a deployed position. The locking device 4180 can include two flexible arms 4181, each having an aperture 4182. The actuator 4136 can include corresponding actuator tabs 4183 that are releasably received in the apertures 4182 to lock the actuator 4136 in one or more selected positions (one is shown in FIG. 41A). The housing can further include a tool aperture 4185 that releasably receives an engaging portion 4162 of an actuator tool 4160. The engaging portion 4162 can further include laterally extending tabs 4165 which are received in corresponding tab slots 4184 of the housing 4140.

Referring now to FIG. 41B, the actuator tool 4160 can be moved axially downwardly to lower the tabs 4165 into the tab slots 4184. Accordingly, the engaging portion 4162 receives the percutaneous probe 4134 and releasably connects with the actuator 4136.

Figure 41C:
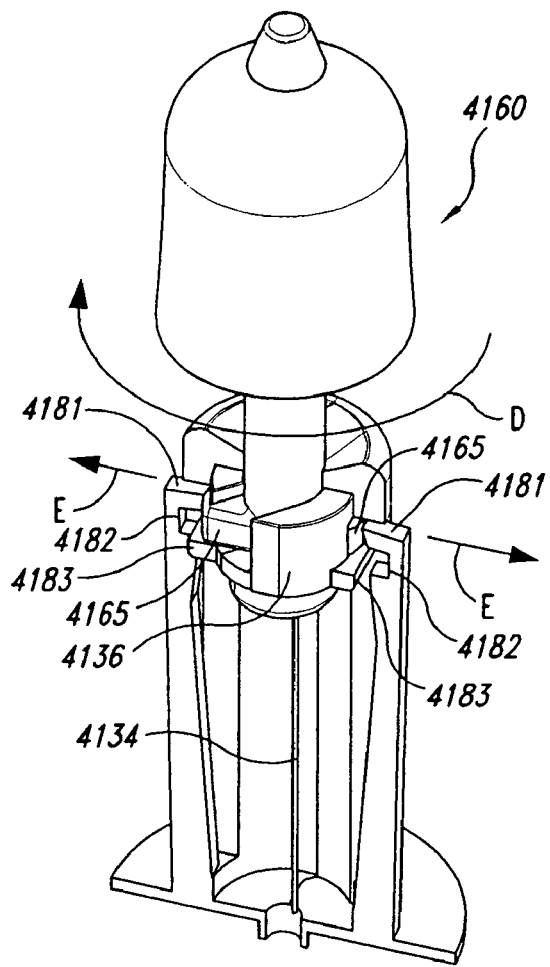

Referring now to FIG. 41C, the actuator tool 4160 can be rotated relative to the actuator 4136, as indicated by arrow D, so that the tabs 4165 engage the flexible arms 4181 of the locking device 4180. As the tabs 4165 engage the flexible arms 4181, they force the flexible arms 4181 laterally outwardly, as indicated by arrows E. As the flexible arms 4181 move laterally outwardly, the aperture 4182 of each arm 4181 moves away from the corresponding actuator tab 4183. Accordingly, the flexible arms 4181 no longer inhibit axial motion of the actuator 4136 relative to the housing 4140.

Figure 41D:
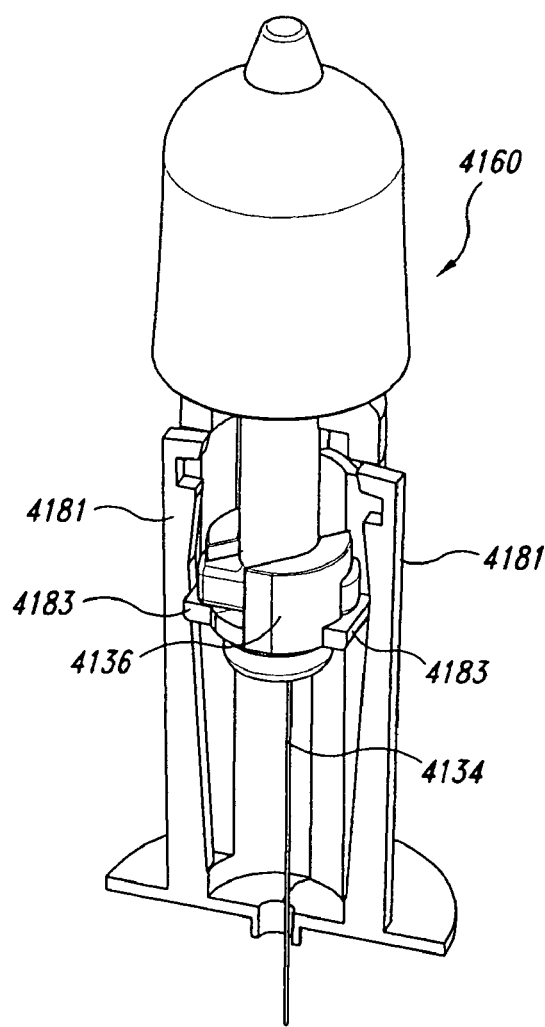

Referring now to FIG. 41D, the actuator 4136 and the percutaneous probe 4134 can be moved axially downwardly by exerting a downward force on the actuator tool 4160. The flexible arms 4181 can return to the position shown in FIG. 41B without interfering with the motion of the actuator 4136. When the percutaneous probe 4134 is returned to its stowed position, the actuator arms 4181 can flex out of the way to allow the actuator 4136 to move axially upwardly. As the actuator tool 4160 is then rotated opposite the direction indicated by arrow D in FIG. 41C, the apertures 4182 of the flexible arms 4181 reengage with the actuator tabs 4183 of the actuator 4136 to once again lock the actuator 4136 from further axial motion.

One feature of the locking devices described above with reference to FIGS. 40A-41D is that they can prevent inadvertent motion of the percutaneous probe relative to the housing, unless the user has properly engaged the actuator tool with the actuator. Accordingly, the percutaneous probe can be less likely to cause inadvertent and potentially harmful pricks to either the practitioner or the recipient.

Another feature of an embodiment of the locking device as described above with reference to FIGS. 40A-40D (and optionally, FIGS. 41A-41D) is that they can be selectively engaged and disengaged at a variety of axial locations to maintain the desired depth of the percutaneous probe once it is deployed. An advantage of that arrangement is that the practitioner will be less likely to inadvertently deploy the percutaneous probe to a greater than desired depth, and can be less likely to withdraw the percutaneous probe unless the actuator tool is properly operated.

Modifications of the above embodiments of the invention will be apparent to those skilled in the art. For example, while aspects of the invention were described in the context of percutaneous electrical therapy in which electrodes are used to deliver electricity to a patient, the sharps-safe features may be used with electrodes designed for medical monitoring and/or diagnosis. In addition, the sharps-safe features of the invention may be used with acupuncture needles or other needles not used for conducting electricity to or from a patient. Many features and advantages of the invention described in the content of particular embodiments are also applicable to other embodiments of the invention. Accordingly, the invention is not limited except as by the appended claims.

We claim:

1. An apparatus for percutaneous application, comprising:
    a housing;
    a percutaneous probe having a sharp end and being positioned within the housing, the percutaneous probe movable relative to the housing between a stowed position and at least one of a first deployed position and a second deployed position, with the percutaneous probe projecting from the housing by a first distance when in the first deployed position, and with the percutaneous probe projecting from the housing by a second distance greater than the first distance when in the second deployed position; and
    a depth control device operatively coupled to the percutaneous probe, the depth control device having a first configuration to allow the percutaneous probe to be moved to the first deployed position, the depth control device having a second configuration to allow the percutaneous probe to be moved to the second deployed position;
    wherein the depth control device includes a tab releasbly coupled to the housing, the tab positioned to at least impede movement of the percutaneous probe when the tab is coupled to the housing.

2. The apparatus of claim 1, further comprising an actuator carrying the percutaneous probe, the actuator being rotatbly supported by the housing, the actuator rotatable between a first positioon with the percutaneous probe in the first deployed position and a second position rotationally spaced apart from the first position with the percutaneous probe in the second deployed position.

3. The apparatus of claim 1, further comprising a locking device positioned to selectively restrict motion of the percutaneous probe when the percutaneous probe is in at least one of the stowed postion, the first deployed postion and the second deployed position.

4. An apparatus for percutaneous application, comprising:
    a housing;
    a percutaneous probe for electrotherapy having a sharp end and being positioned within the housing, the percutaneous probe movable relative to the housing between a stowed position and at least one of a first deployed position and a second deployed position, with the percutaneous probe projecting from the housing by a first distance when in the first deployed position, and with the percutaneous probe projecting from the housing by a second distance greater than the first distance when in the second deployed position; and
    a depth control device operatively coupled to the percutaneous probe, the depth control device having a first configuration to allow the percutaneous probe to be moved to the first deployed position, the depth control device having a second configuration to allow the percutaneous probe to be moved to the second deployed position;

further comprising an actuator carrying the percutaneous probe, the actuator being rotatably supported by the housing, the actuator rotatable between a first position with the percutaneous probe in the first deployed position and a second position rotationally spaced apart from the first position with the percutaneous probe in the second deployed position.

5. An apparatus for percutaneous application, comprising:
a housing;
a percutaneous probe for electrotherapy having a sharp end and being positioned within the housing, the percutaneous probe movable relative to the housing between a stowed position and at least one of a first deployed position and a second deployed position, with the percutaneous probe projecting from the housing by a first distance when in the first deployed position, and with the percutaneous probe projecting from the housing by a second distance greater than the first distance when in the second deployed position; and
a depth control device operatively coupled to the percutaneous probe, the depth control device having a first configuration to allow the percutaneous probe to be moved to the first deployed position, the depth control device having a second configuration to allow the percutaneous probe to be moved to the second deployed position;
further comprising a locking device positioned to selectively restrict motion of the percutaneous probe when the percutaneous probe is in at least one of the stowed position, the first deployed position and the second deployed position.

6. An apparatus for percutaneous application, comprising:
a housing; and
a percutaneous probe having a sharp end and positioned within the housing, the percutaneous probe movable relative to the housing between a stowed position and a deployed position, wherein at least part of the percutaneous probe has a generally non-linear shape when the percutaneous probe is in the stowed position, and wherein the at least part of the percutaneous probe has a generally linear shape when the percutaneous probe is in the deployed position.

7. The apparatus of claim 6, wherein the percutaneous probe is movable to at least one of at least two deployed positions, and wherein the apparatus further comprises a depth control device operatively coupled to the percutaneous probe, the depth control device having a first configuration to allow the percutaneous probe to be moved to a first deployed position, the depth control device having a second configuration to allow the percutaneous probe to be moved to a second deployed position.

8. An apparatus for percutaneous application, comprising:
a housing;
a first percutaneous probe positioned within the housing, the first percutaneous probe having a sharp end and a first percutaneous length, the first percutaneous probe movable relative to the housing between a first stowed position and a first deployed position; and
a second percutaneous probe positioned within the housing simultaneously with the first percutaneous probe, the second percutaneous probe having a sharpened end and a second percutaneous length, the second percuta-
neous probe movable relative to the housing between a second stowed position and a second deployed position;
wherein the housing has an exit portion and an at least partially light transmissive portion positioned proximate to the exit portion, the at least partially light transmissive portion being positioned to allow visual access to the exit portion as the first percutaneous probe is moved to the first deployed position.

9. An apparatus for percutaneous application, comprising:
a housing;
a percutaneous probe for electrotherapy having a sharp end and disposed within the housing, the percutaneous probe being movable relative to the housing between a stowed position and at least one of a first deployed position and a second deployed position, the percutaneous probe having a first deployed length external to the housing when in the first deployed position, the percutaneous probe having a second deployed length external to the housing when in the second deployed position; and
a tool movable relative to the housing, the tool having an engaging portion positioned to selectively engage the percutaneous probe at a first axial location to move the percutaneous probe to the first deployed position, the engaging portion positioned to selectively engage the percutaneous probe at a second axial location spaced apart from the first axial location to move the percutaneous probe to the second deployed position.

10. An apparatus for percutaneous application, comprising:
a housing;
a percutaneous probe having a sharp end and disposed within the housing, the percutaneous probe being movable relative to the housing between a stowed position and at least one of a first deployed position and a second deployed position, the percutaneous probe having a first deployed length external to the housing when in the first deployed position, the percutaneous probe having a second deployed length external to the housing when in the second deployed position; and
a tool movable relative to the housing, the tool having an engaging portion positioned to selectively engage the percutaneous probe at a first axial location to move the percutaneous probe to the first deployed position, the engaging portion positioned to selectively engage the percutaneous probe at a second axial location spaced apart from the first axial location to move the percutaneous probe to the second deployed position;
wherein the engaging portion includes first and second clamp arms pivotable relative to each other to engage and disengage the percutaneous probe.

11. An apparatus for percutaneous application, comprising:
a housing having an exit portion and an at least partially light transmissive portion positioned proximate to the exit portion; and
a percutaneous probe having a sharp end and disposed within the housing, the percutaneous probe movable relative to the housing between a stowed position and a deployed position, with at least part of the percutaneous probe extending out of the housing at the exit portion when the percutaneous probe is in the deployed position, and with the at least partially light transmissive portion positioned to allow visual access to the exit portion as the percutaneous probe moves to the deployed position.

12. The apparatus of claim 11, wherein the at least partially light transmissive portion includes a window opening.

13. The apparatus of claim 11, wherein the percutaneous probe is movable to at least one of two deployed positions, and wherein the apparatus further comprises a depth control device operatively coupled to the percutaneous probe, the depth control device having a first configuration to allow the percutaneous probe to be moved to the first deployed position, the depth control device having a second configuration to allow the percutaneous probe to be moved to the second deployed position.

14. The apparatus of claim 11, wherein at least part of the percutaneous probe has a generally non-linear shape when the percutaneous probe is in the stowed position, and wherein the at least part of the percutaneous probe has a generally linear shape when the percutaneous probe is in the deployed position.

15. An apparatus for percutaneous application, comprising:
    a housing;
    a percutaneous probe having a sharp end and disposed within the housing, the percutaneous probe movable relative to the housing between a stowed position and at least one deployed position;
    a plunger coupled to the probe, the plunger having a handle portion positioned to receive an operator's hand; and
    an electrical coupling in releasable contact with the percutaneous probe, wherein the electrical coupling is removable from the housing independently of the plunger.

16. The apparatus of claim 15, wherein the plunger and the electrical coupling are each movable relative to the housing with the percutaneous probe as the percutaneous probe moves from the stowed position to the at least one deployed position.

17. The apparatus of claim 15, wherein the plunger is movably engaged with the housing to move along a generally helical path as the percutaneous probe moves from the stowed position to the at least one deployed position.

18. An apparatus for percutaneous application, comprising:
    a housing having a first aperture positioned to releasably receive an electrical coupling and a second aperture positioned to receive a plunger;
    a percutaneous probe having a sharp end and disposed within the housing, the percutaneous probe movable relative to the housing between a stowed position and at least one deployed position, the percutaneous probe positioned to releasably contact the electrical coupling; and
    a plunger fixedly coupled to the probe and positioned in the second aperture, the plunger having a handle portion positioned to receive an operator's hand.

19. The apparatus of claim 18, wherein the percutaneous probe is movable to at least one of two deployed positions, and wherein the apparatus further comprises a depth control device operatively coupled to the percutaneous probe, the depth control device having a first configuration to allow the percutaneous probe to be moved to the first deployed position, the depth control device having a second configuration to allow the percutaneous probe to be moved to the second deployed position.

20. A method for operating a percutaneous probe apparatus, comprising:
    choosing a selected deployment depth from at least a first deployment depth and a second deployment depth;
    deploying the percutaneous probe to the selected deployment depth in a recipient's tissue;
    halting deployment of the percutaneous probe at the selected deployment depth with a depth control device of the percutaneous probe apparatus having one of at least two configurations;
    withdrawing the percutaneous probe from the recipient's tissue; and stowing the percutaneous probe in the housing.

21. The method of claim 20, wherein the depth control device includes a pre-adjustable portion configured to be movable between a first stop position and a second stop position without moving the percutaneous probe, and wherein the method further comprises:
    moving the pre-adjustable portion to the first stop position without moving the percutaneous probe; and
    moving the percutaneous probe to the selected deployment depth when the pre-adjustable portion is in the first position.

22. The method of claim 20, further comprising locking the percutaneous probe at the selected deployment depth.

23. A method for operating a percutaneous probe apparatus, comprising:
    choosing a selected deployment depth from at least a first deployment depth and a second deployment depth;
    deploying the percutaneous probe to the selected deployment depth in a recipient's tissue;
    halting deployment of the percutaneous probe at the selected deployment depth with a depth control device of the percutaneous probe apparatus having one of at least two configurations;
    withdrawing the percutaneous probe from the recipient's tissue; and stowing the percutaneous probe in the housing;
    wherein the percutaneous probe is carried by an actuator and wherein the actuator is movable relative to the housing, further wherein one of the actuator and the housing includes first and second detents and the other of the actuator and the housing includes an engaging portion positioned to be selectively engaged with at least one of the first and second detents, and wherein halting motion of the percutaneous probe includes engaging the engaging portion with the first detent.

24. A method for operating a percutaneous probe apparatus, comprising:
    choosing a selected deployment depth from at least a first deployment depth and a second deployment depth;
    deploying the percutaneous probe to the selected deployment depth in a recipient's tissue;
    halting deployment of the percutaneous probe at the selected deployment depth with a depth control device of the percutaneous probe apparatus having one of at least two configurations;
    withdrawing the percutaneous probe from the recipient's tissue; and stowing the percutaneous probe in the housing;
    wherein deploying the percutaneous probe includes rotating an actuator carrying the percutaneous probe to a first of two rotationally spaced apart positions.

25. The method of claim 24, further comprising locking the percutaneous probe at the selected deployment depth.

26. A method for operating a percutaneous probe for electrotherapy, comprising:

stowing the percutaneous probe in a housing with at least part of the percutaneous probe having a generally non-linear shape; and deploying the percutaneous probe into a recipient's tissue with the at least part of the percutaneous probe having a generally linear shape.

27. A method for operating a percutaneous probe, comprising:

stowing the percutaneous probe in a housing with at least part of the percutaneous probe having a generally non-linear shape;

deploying the percutaneous probe into a recipient's tissue with the at least part of the percutaneous probe having a generally linear shape;

choosing a selected deployment depth from at least a first deployment depth and a second deployment depth; and deploying the percutaneous probe to the selected deployment depth in the recipient's tissue by releasably coupling an actuator to the percutaneous probe at one of at least two positions along a length of the percutaneous probe.

28. A method for operating a percutaneous probe for electrotherapy, comprising:

supporting a housing having a percutaneous probe that is movable relative to the housing between a stowed position, a first deployed position and a second deployed position, the percutaneous probe having a first deployed length external to the housing when in the first deployed position, the percutaneous probe having a second deployed length external to the housing when in the second deployed position;

selecting either one of the first and second deployed positions;

deploying the percutaneous probe from the housing to the one of the first and second deployed positions; and halting movement of the percutaneous probe beyond the at least one of the first and second positions.

29. A method for operating a percutaneous probe, comprising:

supporting a housing having a percutaneous probe that is movable relative to the housing between a stowed position, a first deployed position and a second deployed position, the percutaneous probe having a first deployed length external to the housing when in the first deployed position, the percutaneous probe having a second deployed length external to the housing when in the second deployed position;

selecting either one of the first and second deployed positions;

deploying the percutaneous probe from the housing to the one of the first and second deployed positions; and halting movement of the percutaneous probe beyond the at least one of the first and second positions; and releasably engaging a tool with the percutaneous probe at one of two axial locations of the percutaneous probe, with a first axial location corresponding to the first deployed position and a second axial location spaced apart from the first axial location and corresponding to the second deployed position.

30. A method for operating a percutaneous probe, comprising:

supporting a housing having a percutaneous probe that is movable relative to the housing between a stowed position, a first deployed position and a second deployed position, the percutaneous probe having a first deployed length external to the housing when in the first deployed position, the percutaneous probe having a second deployed length external to the housing when in the second deployed position;

selecting either one of the first and second deployed positions;

deploying the percutaneous probe from the housing to the one of the first and second deployed positions; and halting movement of the percutaneous probe beyond the at least one of the first and second positions; and releasably clamping a portion of a tool around the percutaneous probe at one of two axial locations of the percutaneous probe, with a first axial location corresponding to the first deployed position and a second axial location spaced apart from the first axial location and corresponding to the second deployed position.

31. A method for operating a percutaneous probe, comprising:

releasably attaching to a recipient's skin a housing having a percutaneous probe and an exit portion through which the percutaneous probe exits the housing; and deploying a sharp end of the percutaneous probe from the housing into the recipient's skin while visually accessing the exit portion through an at least partially light transmissive portion of the housing.

32. A method for operating a percutaneous probe, comprising:

supporting a housing having a percutaneous probe, the percutaneous probe movable relative to the housing between a stowed position and at least one deployed position, the percutaneous probe coupled to a plunger;

releasably connecting an electrical coupling to the percutaneous probe, wherein the electrical coupling is removable from the housing independently of the plunger; and deploying the percutaneous probe by moving the plunger relative to the housing.

33. The method of claim 32, wherein moving the plunger includes moving the plunger along a generally helical path, and wherein the method further comprises carrying the electrical coupling along a generally linear path with at least one of the percutaneous probe and the plunger as the plunger moves relative to the housing.

34. A method for deploying a percutaneous probe, comprising:

engaging with a recipient's skin a housing having a percutaneous probe that is movable relative to the housing between a stowed position and at least one deployed position, the housing further having an attachment device configured to be releasably attached to the recipient's skin, the housing further having an external housing surface extending away from the attachment device and facing outwardly transverse to the attachment device;

releasably attaching the attachment device to the recipient's skin;

releasably coupling an actuator tool with the percutaneous probe;

releasably gripping a gripping portion of the actuator tool; and deploying the percutaneous probe into the recipient's skin by moving the actuator tool at least until the gripping portion is adjacent to and laterally offset from the external housing surface.

35. The method of claim 34, further comprising:
choosing a selected deployment depth from at least a first deployment depth and a second deployment depth;
deploying the percutaneous probe to the selected deployment depth in a recipient's tissue;
halting deployment of the percutaneous probe at the selected deployment depth with a depth control device of the percutaneous probe apparatus having one of at least two configurations;
withdrawing the percutaneous probe from the recipient's tissue; and
stowing the percutaneous probe in the housing.

* * * * *